US008835021B2

(12) United States Patent
Yersin et al.

(10) Patent No.: US 8,835,021 B2
(45) Date of Patent: Sep. 16, 2014

(54) MATERIALS FOR ORGANIC ELECTROLUMINESCENCE DEVICES

(75) Inventors: Hartmut Yersin, Sinzing (DE); Uwe Monkowius, Linz (AT); Rafal Czerwieniec, Obertraubling (DE); Jiangbo Yu, Clemson, SC (US)

(73) Assignee: Merck Patent GmbH, Darmstadt (DE)

( * ) Notice: Subject to any disclaimer, the term of this patent is extended or adjusted under 35 U.S.C. 154(b) by 542 days.

(21) Appl. No.: 13/001,719

(22) PCT Filed: Aug. 25, 2009

(86) PCT No.: PCT/EP2009/006149
§ 371 (c)(1),
(2), (4) Date: Mar. 8, 2011

(87) PCT Pub. No.: WO2010/031485
PCT Pub. Date: Mar. 25, 2010

(65) Prior Publication Data
US 2011/0155954 A1 Jun. 30, 2011

(30) Foreign Application Priority Data
Sep. 22, 2008 (DE) .......................... 10 2008 048 336

(51) Int. Cl.
| H01L 51/54 | (2006.01) |
| C09K 11/06 | (2006.01) |
| H01L 51/00 | (2006.01) |
| C07F 5/02 | (2006.01) |
| C09B 57/10 | (2006.01) |
| H01L 51/50 | (2006.01) |

(52) U.S. Cl.
CPC ...... *H01L 51/0091* (2013.01); *C09K 2211/188* (2013.01); *C09K 11/06* (2013.01); *C09K 2211/1044* (2013.01); *C09K 2211/1085* (2013.01); *C07F 5/02* (2013.01); *H01L 51/0037* (2013.01); *H01L 51/008* (2013.01); *H01L 51/0094* (2013.01); *H01L 51/5012* (2013.01); *H01L 2251/5384* (2013.01); *C09B 57/10* (2013.01); *Y02E 10/549* (2013.01); *Y10S 428/917* (2013.01)
USPC ........... 428/690; 428/917; 313/504; 313/506; 252/301.16; 257/40; 257/E51.044

(58) Field of Classification Search
CPC ..................................... C07F 1/08; C07F 5/02
See application file for complete search history.

(56) References Cited

U.S. PATENT DOCUMENTS

| 5,627,164 | A | 5/1997 | Gorun et al. |
| 6,649,801 | B2 | 11/2003 | Peters et al. |
| 6,989,273 | B2 | 1/2006 | Hsieh et al. |
| 7,345,301 | B2 | 3/2008 | Gerhard et al. |
| 7,701,131 | B2 | 4/2010 | Gerhard et al. |
| 7,795,801 | B2 | 9/2010 | Ueda et al. |
| 7,820,305 | B2 | 10/2010 | Schulte et al. |
| 2002/0179885 | A1 | 12/2002 | Che et al. |
| 2002/0182441 | A1 | 12/2002 | Lamansky et al. |
| 2003/0186080 | A1 | 10/2003 | Kamatani et al. |
| 2003/0205707 | A1 | 11/2003 | Chi-Ming |
| 2005/0069729 | A1 | 3/2005 | Ueda et al. |
| 2005/0221115 | A1 | 10/2005 | Tsuboyama et al. |
| 2005/0249970 | A1 | 11/2005 | Suzuri et al. |
| 2006/0058494 | A1 | 3/2006 | Busing et al. |
| 2006/0258043 | A1 | 11/2006 | Bold et al. |
| 2007/0111025 | A1 | 5/2007 | Lennartz et al. |
| 2007/0135635 | A1 | 6/2007 | Stössel et al. |
| 2007/0176147 | A1 | 8/2007 | Buesing et al. |
| 2008/0199731 | A1 | 8/2008 | Vogler et al. |
| 2009/0134384 | A1 | 5/2009 | Stoessel et al. |
| 2009/0167166 | A1 | 7/2009 | Bach et al. |
| 2009/0302742 | A1 | 12/2009 | Komori et al. |
| 2009/0302752 | A1 | 12/2009 | Parham et al. |
| 2010/0059740 | A1 | 3/2010 | Yersin et al. |
| 2010/0176386 | A1 | 7/2010 | Yersin et al. |
| 2010/0187977 | A1 | 7/2010 | Kai et al. |
| 2010/0244009 | A1 | 9/2010 | Parham et al. |

FOREIGN PATENT DOCUMENTS

| CN | 1624070 A | 6/2005 |
| DE | 10338550 A1 | 3/2005 |
| DE | 10350606 A1 | 6/2005 |
| DE | 10358665 A1 | 7/2005 |
| DE | 102008036982 A1 | 8/2008 |
| DE | 102008056688 A1 | 11/2008 |
| DE | 102008033943 A1 | 1/2010 |
| EP | 0652273 A1 | 5/1995 |
| EP | 1205527 A1 | 5/2002 |
| EP | 1617710 A1 | 1/2006 |
| EP | 1617711 A1 | 1/2006 |
| EP | 1731584 A1 | 12/2006 |
| JP | 2004-288381 A | 10/2004 |

(Continued)

OTHER PUBLICATIONS

McCormick et al. "Phosphorescent Cu(I) complexes of 2-(2'-pyridylbenzimidazolyl)benzene: impact of phosphine ancillary ligands on electronic and photophysical properties of the Cu(I) complexes." Inorg. Chem. vol. 45, No. 1, pp. 147-155, 2006.*
Monkowius et al. "Synthesis, characterization and ligand properties of novel bi-1,2,3-triazole ligands." Eur. J. Inorg. Chem. 2007, pp. 4597-4606.*
Armaroli, et al., "Highly Luminescent Cu$^I$ Complexes for Light-Emitting Electrochemical Cells," Adv. Mater., vol. 18, pp. 1313-1316 (2006).

(Continued)

*Primary Examiner* — Michael H Wilson
(74) *Attorney, Agent, or Firm* — Drinker Biddle & Reath LLP

(57) ABSTRACT

The invention relates to mononuclear, neutral copper (1) complexes having a bidentate ligand that binds via nitrogen, and two phosphane or arsane ligands, to the use thereof for producing electronic components, and to electronic devices comprising said complexes.

15 Claims, 8 Drawing Sheets

(56) References Cited

FOREIGN PATENT DOCUMENTS

| | | | |
|---|---|---|---|
| JP | 2005-347160 A | 12/2005 | |
| JP | 2006228936 A | 8/2006 | |
| WO | WO-03/095587 A1 | 11/2003 | |
| WO | WO-2004/013080 A1 | 2/2004 | |
| WO | WO-2004/016711 A1 | 2/2004 | |
| WO | WO-2004/017043 A2 | 2/2004 | |
| WO | WO-2004/037887 A2 | 5/2004 | |
| WO | WO-2004/093207 A2 | 10/2004 | |
| WO | WO-2005/011013 A1 | 2/2005 | |
| WO | WO-2005/039246 A1 | 4/2005 | |
| WO | WO-2005/054404 A1 | 6/2005 | |
| WO | WO-2005/111172 A2 | 11/2005 | |
| WO | WO-2005/118606 A1 | 12/2005 | |
| WO | WO-2006/003000 A1 | 1/2006 | |
| WO | WO-2006/005627 A1 | 1/2006 | |
| WO | WO-2006/028546 A1 | 3/2006 | |
| WO | WO-2006/032449 A1 | 3/2006 | |
| WO | WO-2006/117052 A1 | 11/2006 | |
| WO | WO-2007/063754 A1 | 6/2007 | |
| WO | WO-2007/137725 A1 | 12/2007 | |
| WO | WO-2008/056746 A1 | 5/2008 | |
| WO | WO-2008/086851 A1 | 7/2008 | |
| WO | WO-2008/087031 A1 | 7/2008 | |
| WO | WO 2009/000673 A2 * | 12/2008 | ............ C07K 11/58 |
| WO | WO-2009/003700 A1 | 1/2009 | |
| WO | WO-2009/062578 A1 | 5/2009 | |
| WO | WO-2010/006680 A1 | 1/2010 | |
| WO | WO-2010/015306 A1 | 2/2010 | |
| WO | WO-2010/054729 A3 | 5/2010 | |

OTHER PUBLICATIONS

Zhang, et al., "Highly Efficient Green Phosphorescent Organic Light-Emitting Diodes Based on $Cu^I$ Complexes," *Adv. Mater.*, vol. 16, No. 5, pp. 432-436 (2004).

Monkowius, et al., "Synthesis, Crystal Structures, and Electronic Spectra of (1,8-naphthyridine)$Re^I(CO)_3Cl$ and [(1,8-naphthyridine)$Cu^I$(DPEPhos)]$PF_6$," *Inorganic Chemistry Communications*, vol. 20, pp. 1473-1477 (2007).

Marzano, et al., "Synthesis, Characterization, and in Vitro Antitumor Properties of Tris(hydroxymethyl)phosphine Copper(I) Complexes Containing the New Bis(1,2,4-triazol-1-yl)acetate Ligand," *J. Med. Chem.*, vol. 49, pp. 7317-7324 (2006).

Dou, et al., "Synthesis and Crystal Structure of Three Carborane Complexes, [M{7,8-$(OPPh_2)2$-7,8-$C_2B_9H_{10}$}2] (M=Cu, Zn) and [Ni(thf){7,8-$(OPPh_2)_2$-7,8-$C_2B_9H_{10}$}2]•thf, and Two Carbine Compounds, 1-$(OPPh_2)$-$_2$-$(PPh_2)$-1,2-$C_2B_{10}H_{10}$ and H[7,8-$(OPPh_2)_2$-7,8-$C_2B_9H_{10}$]•0.25$C_2H_5OH$," *Eur. J. Inorg. Chem.*, pp. 53-59 (2007).

Lobbia, et al., "Copper(I) Coordination Polymers and Mononuclear Copper (I) Complexes Built from Poly(1,2,4-triazolyl)borate ligands and Tri-organophosphines," *J. Chem. Soc., Dalton Trans.*, pp. 2333-2340 (2002).

Marzano, et al., "New Copper(I) Phosphane Complexes of Dihydridobis(3-nitro-1,2,4-triazolyl)borate Ligand Showing Cytotoxic Activity," *Journal of Inorganic Biochemistry*, vol. 100, pp. 299-304 (2006).

\* cited by examiner

Figure 4
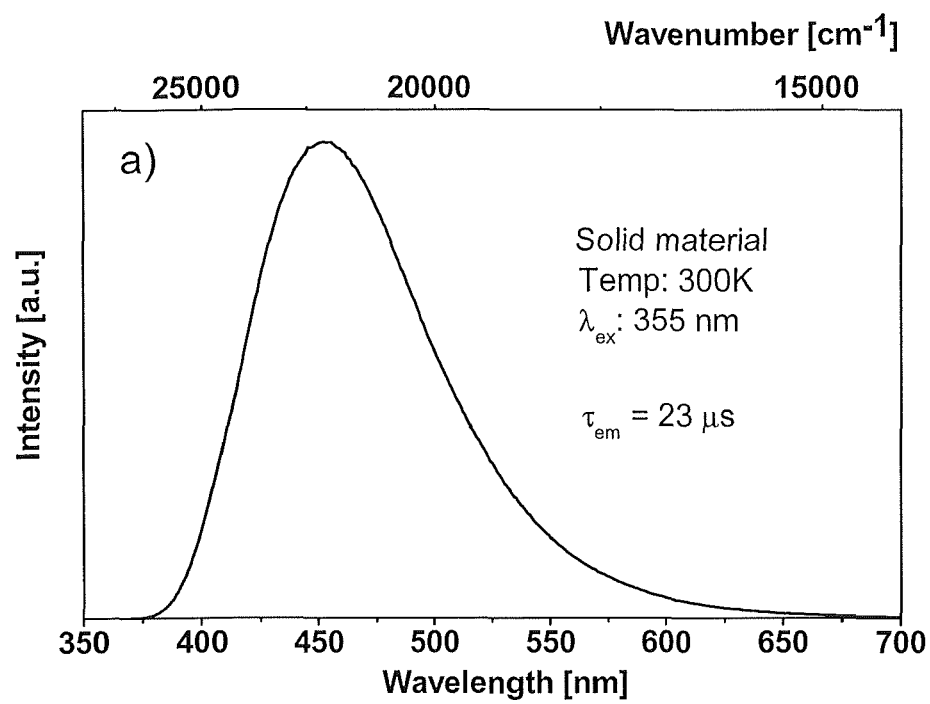
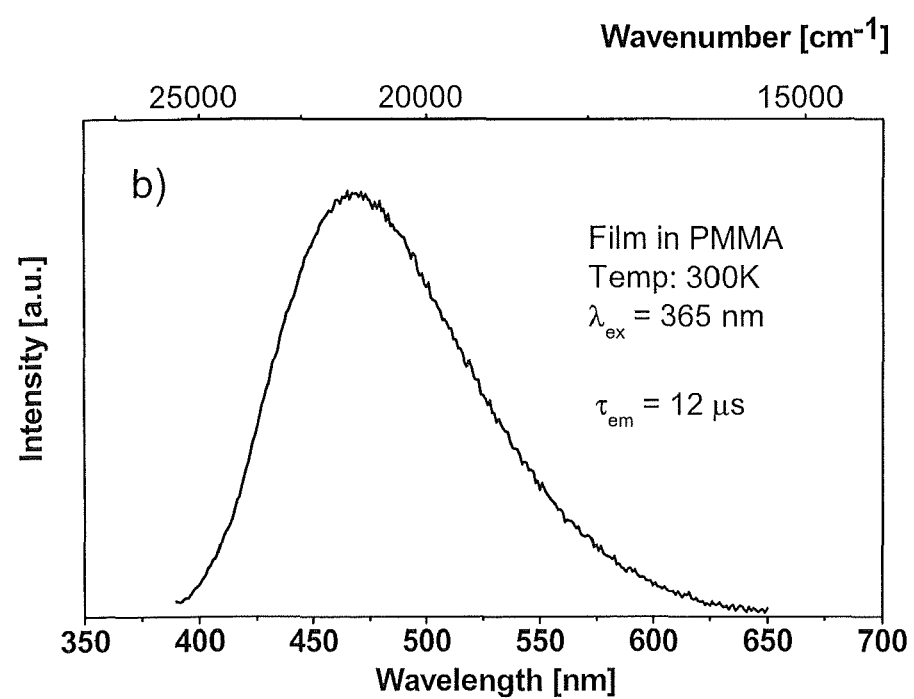

Figure 11

| 7 | Cathode, Al: 60 nm |
| 6 | Interlayer CsF: 0.8 nm |
| 5 | ETL, Alq$_3$: 40 nm |
| 4 | Emitter layer: 30 to 100 nm |
| 3 | HTL, PEDOT: PSS: 50 nm |
| 2 | Anode, ITO: 40 nm |
| 1 | Support material, glass |

Figure 12

| Layer | Thickness |
|---|---|
| Cathode: Al | 200 nm |
| Interlayer: LiF | 0.8 nm |
| Electron-transport layer ETL: Alq$_3$ | 40 nm |
| Emitter layer EML: UGH with 6% complex doping | 70 nm |
| Hole-transport layer HTL: α-NPD | 30 nm |
| Hole-injection layer HIL: CuPc | 10 nm |
| Anode ITO | 40 nm |
| Support material glass | |

ETL = electron-transport layer

EML = emitter layer

HTL = hole-transport layer

HIL = hole-injection layer

Alq$_3$ = aluminium 8-hydroxyquinoline

α-NPD = 4,4'-bis[N-(1-naphthyl)-N-phenylamino]biphenyl

CuPc = copper phthalocyanine

UGH = ultrahigh gap host matrix material having a large energy gap

ITO = indium tin oxide

Figure 13

| 9 | Cathode |
|---|---|
| 8 | Interlayer |
| 7 | ETL |
| 6 | Hole-blocking layer |
| 5 | Emitter layer |
| 4 | Electron-blocking layer |
| 3 | HTL |
| 2 | Anode, ITO |
| 1 | Support material, glass |

MATERIALS FOR ORGANIC ELECTROLUMINESCENCE DEVICES

RELATED APPLICATION

This application is a national stage application (under 35 U.S.C. §371) of PCT/EP2009/006149, filed Aug. 25, 2009, which claims benefit of German Application No. 10 2008 048 336.2, filed Sep. 22, 2008.

The invention relates to mononuclear neutral copper(I) complexes of the formula A ([(N∩N)CuL$_2$]) and to the use thereof for the production of opto-electronic components,

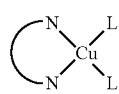

formula A where N∩N stands for a chelating N-heterocyclic ligand, which is bonded to the copper atom via two nitrogen atoms, and L is, independently of one another, a phosphine or arsine ligand. The two ligands L may also be bonded to one another, giving rise to a divalent ligand. In this case, either a) N∩N must be mononegative and the two ligands (phosphine or arsine ligands) must be neutral (preferred embodiment) or b) N∩N must be neutral and the two phosphine/arsine ligands taken together must be mono-negatively charged, so that the mononuclear copper(I) complex is electrically neutral.

INTRODUCTION

A change is currently evident in the area of display screen and illumination technology. It will be possible to manufacture flat displays or lighting areas with a thickness of less than 0.5 mm. These are distinguished by many fascinating properties. Thus, for example, it will be possible to develop lighting areas as wallpapers having very low energy consumption. However, it is particularly interesting that it will be possible to produce colour display screens having hitherto unachievable colour fidelity, brightness and viewing-angle independence, having low weight and very low power consumption. It will be possible to design the display screens as microdisplays or large display screens having an area of several m$^2$ in rigid or flexible form, but also as transmission or reflection displays. It is furthermore possible to employ simple and cost-saving production processes, such as screen printing, ink-jet printing or vacuum sublimation. This will facilitate very inexpensive manufacture compared with conventional flat display screens. This novel technology is based on the principle of OLEDs, Organic Light Emitting Devices.

Components of this type consist predominantly of organic layers, as shown diagrammatically and in a simplified manner in FIG. 1. At a voltage of, for example, 5 V to 10 V, negative electrons exit from a conducting metal layer, for example an aluminium cathode, into a thin electron-conduction layer and migrate in the direction of the positive anode. The latter consists, for example, of a transparent, electrically conductive, thin indium tin oxide layer, from which positive charge carriers ("holes") migrate into an organic hole-conduction layer. These holes move in the opposite direction compared with the electrons, more precisely towards the negative cathode. A central layer, the emitter layer, which likewise consists of an organic material, additionally contains special emitter molecules, at which or in the vicinity of which the two charge carriers recombine and result in energetically excited states of the emitter molecules. The excited states then release their energy as light emission. It may also be possible to omit a separate emitter layer if the emitter molecules are located in the hole- or electron-conduction layer.

The OLED components can have a large-area design as illumination elements or an extremely small design as pixels for displays. The crucial factor for the construction of highly efficient OLEDs is the light-emitting materials used (emitter molecules). These can be achieved in various ways, using organic or organometallic compounds. It can be shown that the light yield of the OLEDs can be significantly greater with organometallic substances, so-called triplet emitters, than with purely organic emitter materials. Owing to this property, the further development of organometallic materials is of essential importance. The function of OLEDs has already been described very frequently [i-vi]. A particularly high efficiency of the device can be achieved using organometallic complexes having a high emission quantum yield. These materials are frequently referred to as triplet emitters or phosphorescent emitters. This knowledge has been known for some time [i-v]. Many protective rights have already been applied for or granted for triplet emitters [vii-xix].

Triplet emitters have great potential for the generation of light in displays (as pixels) and in illumination areas (for example as light-emitting wallpaper). A very large number of triplet emitter materials have already been patented and are in the meantime also being employed technologically in first devices. The solutions to date have disadvantages/problems, more precisely in the following areas:

long-term stability of the emitters in the OLED devices, thermal stability, chemical stability to water and oxygen, chemical variability, availability of important emission colours, manufacturing reproducibility, achievability of high efficiencies of the conversion of electrical current into light, achievability of very high luminous densities at the same time as high efficiency, use of inexpensive emitter materials, toxicity of the materials used/disposal of used light-emitting elements, development of blue-emitting OLEDs.

Organometallic triplet emitters have already successfully been employed as emitter materials in OLEDs. In particular, it has been possible to construct very efficient OLEDs with red- and green-luminescent triplet emitters. However, the production of blue-emitting OLEDs continues to encounter considerable difficulties. Besides the lack of suitable matrix materials for the emitters, suitable hole- and/or electron-conducting matrix materials, one of the main difficulties is that the number of usable triplet emitters known to date is very limited. Since the energy separation between the lowest triplet state and the ground state for blue-luminescent triplet emitters is very large, the emission is often quenched intramolecularly by thermal occupation of non-emitting, excited states, in particular the metal-centred dd* states. In previous attempts to produce blue-emitting OLEDs, predominantly organometallic compounds from the platinum group were employed, for example Pt(II), Ir(III), Os(II). Some structural formulae (1 to 4) are depicted below by way of example.

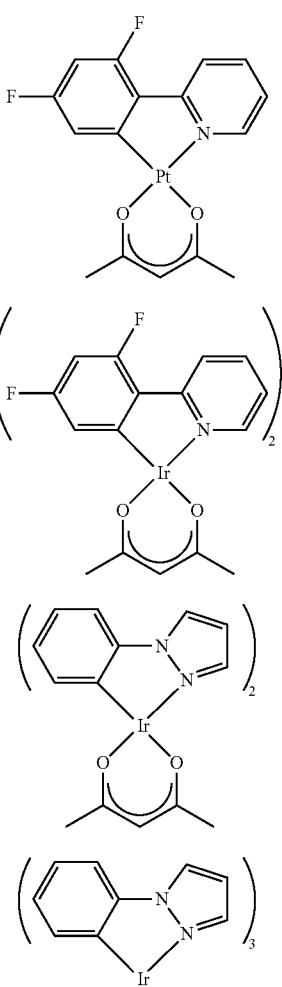

However, the blue-emitting triplet emitters used to date are disadvantageous in a number of respects. In particular, the synthesis of such compounds requires complex, multistep (for example two or more steps) and time-consuming reactions. In addition, the syntheses of such organometallic compounds are frequently carried out at very high temperatures (for example T≥100° C.) in organic solvents. In spite of the great synthetic complexity, only moderate to poor yields are frequently achieved. Since, in addition, rare noble-metal salts are used for the synthesis, very high prices (in the order of €1000/g) of the blue-emitting triplet emitters obtainable to date are the consequence. In addition, the emission quantum yields are in some cases still low, and there is a need for improvement in the long-term chemical stability of the materials.

An alternative to such organometallic compounds from the platinum group may be the use of organometallic complexes of other, cheaper transition metals, in particular of copper. Luminescent copper(I) complexes have already been known for some time, for example copper(I) complexes with aromatic diimine ligands (for example 1,10-phenanthrolines) have intense red photoluminescence [xx]. Likewise, a large number of binuclear and polynuclear copper(I) complexes with N-heteroaromatic [xxi] and/or phosphine ligands [xxii, xxiii,xxiv] which exhibit intense luminescence has already been described.

Some copper(I) complexes have already been proposed as OLED emitter materials. JP 2006/228936 (I. Toshihiro) describes the use of binuclear and trinuclear Cu, Ag, Hg and Pt complexes with nitrogen-containing heteroaromatic ligands, in particular with substituted pyrazoles. WO 2006/032449 A1 (A. Vogler et al.) has described the use of mononuclear copper(I) complexes with a tridentate trisphosphine ligand and a small anionic ligand (for example halogen, CN, SCN, etc.). Contrary to what has been postulated [xxv], however, this is very probably a binuclear complex [xxvi]. Electroluminescent copper(I) complexes with diimine ligands (for example 1,10-phenanthroline) have been proposed in US 2005/0221115 A1 (A. Tsuboyama et al.), as have organic polymers to which complexes of this type are attached. Various copper(I)/diimine complexes and copper clusters [xxvii] as green and red triplet emitters in OLEDs and LECs [xxviii] (light-emitting electrochemical cells) have likewise been described [xxix]. Binuclear Cu complexes with bridging, bidentate ligands are described in WO 2005/054404 A1 (A. Tsuboyama et al.).

DESCRIPTION OF THE INVENTION

The present invention relates to mononuclear, neutral copper(I) complexes of the formula A and to the use thereof in opto-electronic components.

formula A

In formula A (also referred to as [(N∩N)CuL$_2$] below), N∩N stands for a chelating N-heterocyclic ligand, which is bonded to the copper centre via two nitrogen atoms, and L stands, independently of one another, for a phosphine or arsine ligand, where the two ligands L may also be bonded to one another, giving rise to a divalent ligand, or where one ligand L or both ligands L may also be bonded to N∩N, giving rise to a trivalent or tetra-valent ligand. In this case, either a) N∩N must be mononegative and the two ligands L (phosphine and/or arsine ligands) must be neutral (preferred embodiment) or b) N∩N must be neutral and the two ligands L (phosphine and/or arsine ligands) taken together must be mononegatively charged, so that the copper(I) complex of the formula A overall is electrically neutral.

Specific embodiments of the mononuclear, neutral copper (I) complexes of the formula A according to the invention are represented by the compounds of the formulae I to IX and are explained below.

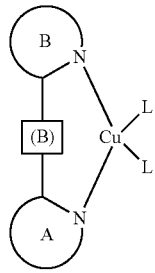

formula I

-continued

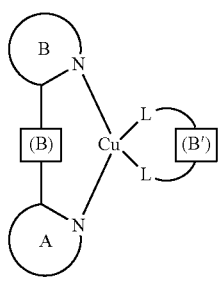
formula II

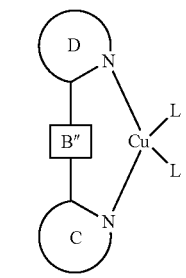
formula III

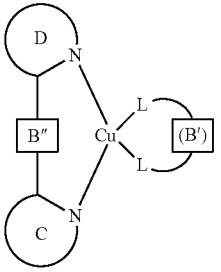
formula IV

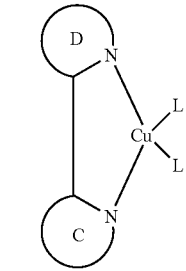
formula V

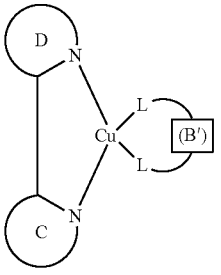
formula VI

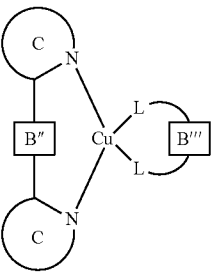
formula VII

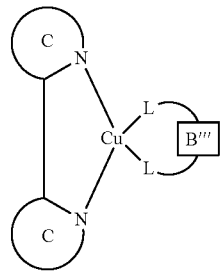
formula VIII

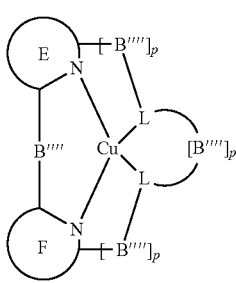
formula IX

The meaning of the symbols and indices used in the formulae I to IX is explained below.

Many of the copper complexes presented to date usually have the disadvantage of not being neutral, but instead being charged. In some cases, this results in problems during the production and operation of the usual opto-electronic components. For example, the lack of volatility of charged complexes prevents application by vacuum sublimation, and charged emitters could result in undesired ion migration during operation of a conventional OLED due to the high electrical field strengths.

The neutrality of the copper(I) complexes of the formulae I to IX is in all cases given since Cu(I) is monopositively charged and one of the ligands is mononegatively charged. The mononuclear neutral copper(I) complexes according to the invention accordingly have one mononegatively charged ligand and one neutral ligand.

In order that the complexes are suitable as blue triplet emitters for OLEDs, their $S_0$-$T_1$ energy separations must be sufficiently large ($S_0$=electronic ground state, $T_1$=lowest excited triplet state). The energy separations should be greater than 22,000 cm$^{-1}$, preferably greater than 25,000 cm$^{-1}$. This requirement is satisfied by the complexes of the present invention. Complexes having a smaller $S_0$-$T_1$ energy separation are also suitable for green or red emission.

A) Anionic Ligands N—B—N and Neutral Ligands L or L-B'-L (Phosphines and Arsines, Monovalent or Divalent)

Preference is given to complexes of the formulae I and II, namely formula I

-continued

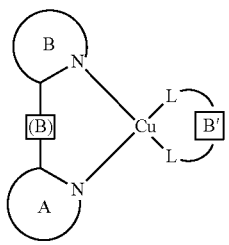

formula II with a mononegatively charged ligand, so that the monopositive charge of the Cu(I) central ion is neutralised. In these formulae,

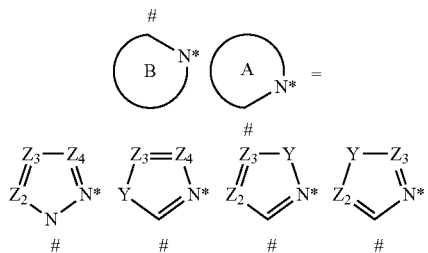

where
$Z_2$-$Z_4$ are on each occurrence, identically or differently, N or CR;
R is on each occurrence selected, identically or differently, from the group consisting of H, D, F, Cl, Br, I, CN, NO$_2$, N(R$^1$)$_2$, C(=O)R$^1$, Si(R$^1$)$_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^1$, where one or more non-adjacent CH$_2$ groups may be replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, O, S or CONR$^1$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^1$, an aryloxy or heteroaryloxy group having 5 to 60 aromatic ring atoms, which may be substituted by one or more radicals R$^1$, or a combination of these systems, where two or more adjacent substituents R may optionally form a monocyclic or polycyclic, aliphatic, aromatic or heteroaromatic ring system, which may be substituted by one or more radicals R$^1$;
R$^1$ is on each occurrence selected, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R$^3$ may form a mono- or polycyclic, aliphatic, aromatic or heteroaromatic ring system with one another;
Y is on each occurrence, identically or differently, O, S or NR;
(B) is R$_2$B, where R has the meaning mentioned above, for example H$_2$B, Ph$_2$B, Me$_2$B, ((R$^1$)$_2$N)$_2$B etc. (where Ph=phenyl, Me=methyl), and where B stands for boron;
"*" denotes the atom which forms the complex bond; and
"#" denotes the atom which is bonded to the second unit via B.

These ligands will be referred to as N—B—N below.

The following examples are intended to illustrate these ligands:

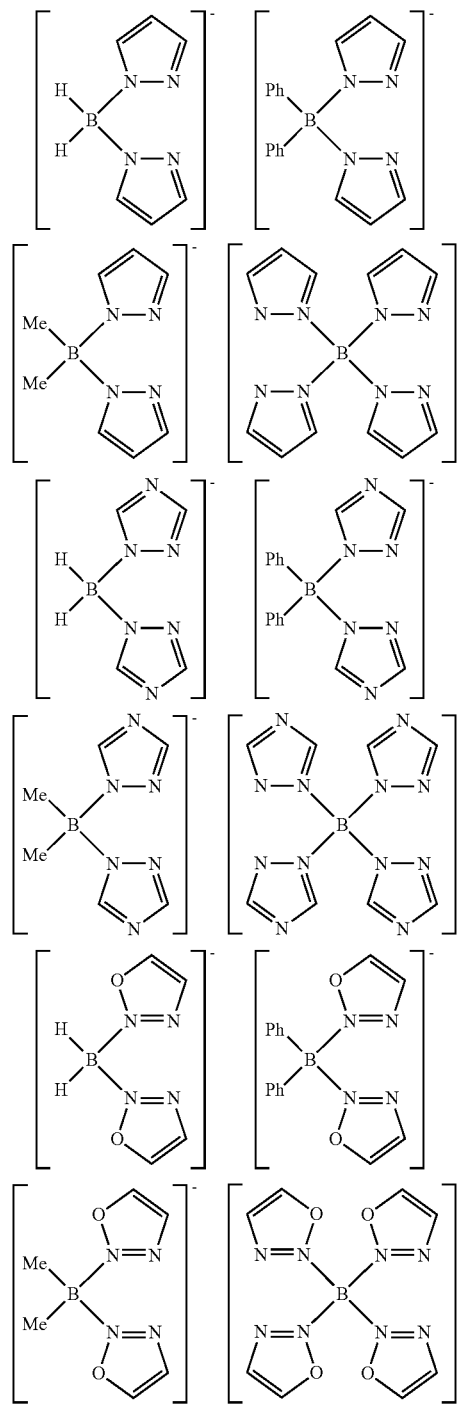

These structures may also be substituted by one or more radicals R.

In addition, the anionic ligands of the formulae III to VI can also be a nitrogen ligand of the general formula:

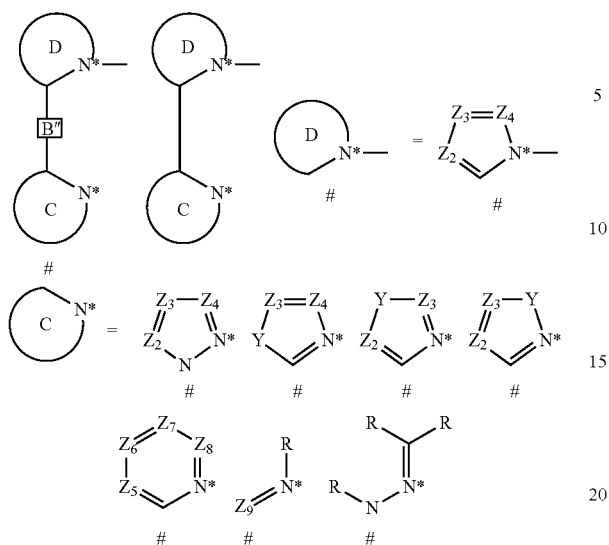

where $Z_2$-$Z_9$ have the same meaning as defined above for $Z_2$-$Z_4$, and where R, Y and the symbols "*" and "#" have the same meaning as defined above, and furthermore:

B″ is a neutral bridge, in particular is on each occurrence, identically or differently, a divalent bridge selected from NR, BR, O, $CR_2$, $SiR_2$, C=NR, C=$CR_2$, S, S=O, $SO_2$, PR and P(=O)R.

Nitrogen ligands which contain the bridge B″ will be referred to as N—B″—N below, and those which do not contain the bridge will be referred to as N∩N.

The following examples are intended to illustrate these ligands:

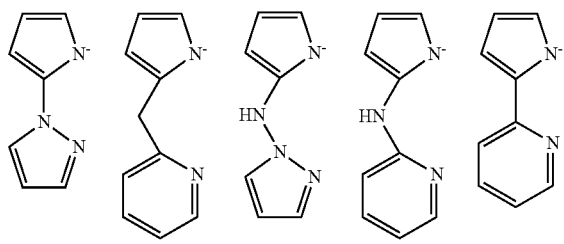 [SMILES: c1c[n-]c(-n2cccn2)c1 ; c1ccc(Cc2ccc[n-]2)nc1 ; c1c[n-]c(Nn2cccn2)c1 ; c1ccc(Nc2ccc[n-]2)nc1 ; c1ccc(-c2ccc[n-]2)nc1]

These structures may also be substituted by one or more radicals R.

Complexes of the general formulae III to VI thus arise:

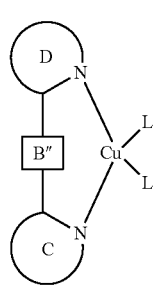

formula III

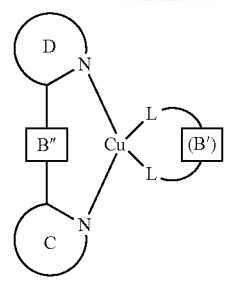

formula IV

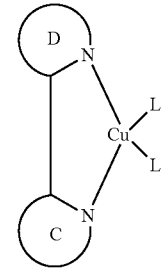

formula V

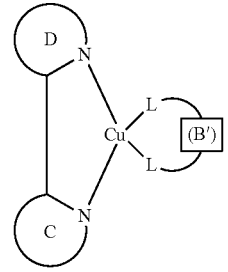

formula VI where:
L is a monodentate phosphine or arsine ligand $R_3E$ (where E=P or As);
L-B′-L is a phosphanyl or arsanyl radical ($R_2$E#, where E=P or As), which is bonded to a further radical L via a bridge B′ and thus forms a bidentate ligand; and
B′ is an alkylene or arylene group or a combination of the two, or —O—, —NR— or —$SiR_2$—.

In a preferred embodiment of the invention, E is equal to phosphorus.

The following examples are intended to illustrate this:
Examples of L:
$Ph_3P$, $Me_3P$, $Et_3P$, $Ph_2MeP$, $Ph_2BnP$, (cyclohexyl)$_3$P, (PhO)$_3$P, (MeO)$_3$P, $Ph_3As$, $Me_3As$, $Et_3As$, $Ph_2MeAs$, $Ph_2BnAs$, (cyclohexyl)$_3$As (Ph=phenyl, Me=methyl, Et=ethyl, Bn=benzyl).
Examples of L-B′-L:

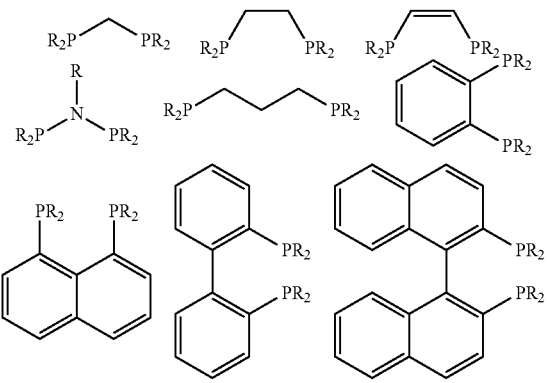

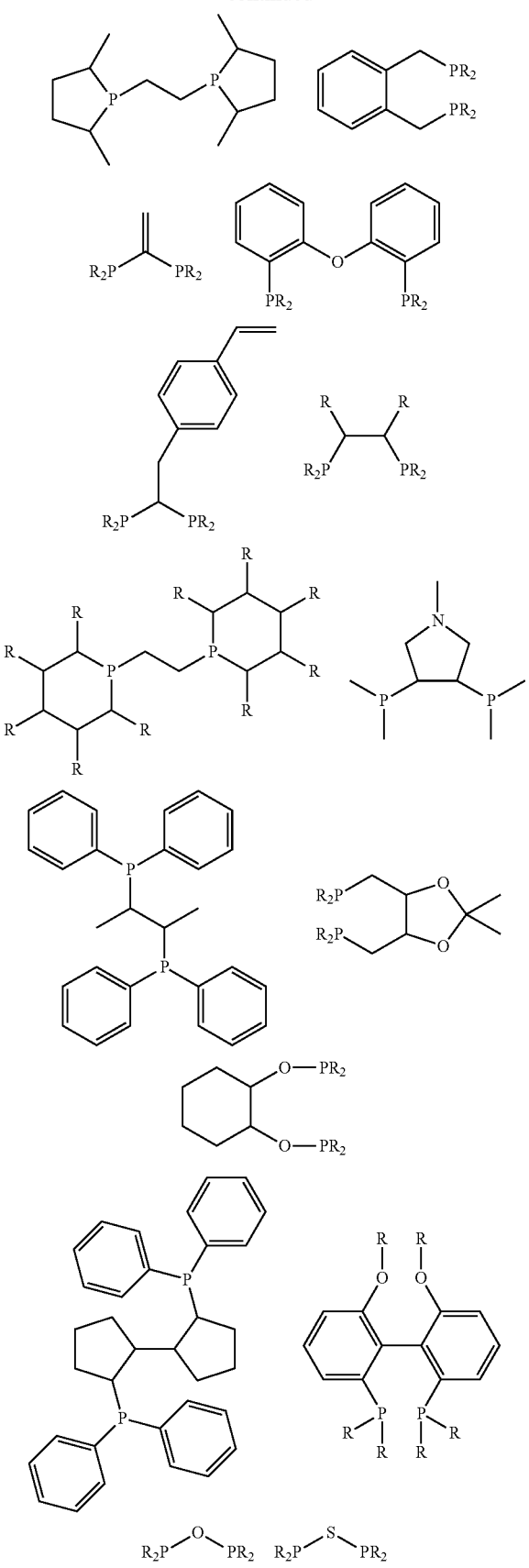

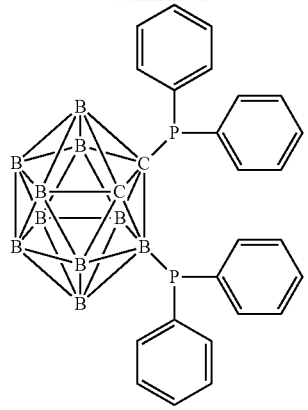

etc.

The ligands L and L-B'-L here may also be substituted by one or more radicals R, where R has the meaning mentioned above.

B) Neutral Ligands N—B"—N and Anionic Ligands L-B'"-L

As already stated above, Cu(I) complexes of the form [(N∩N)Cu(R₃P)₂]An or [(N∩N)Cu(P∩P)]An[(N∩N)=diimine ligand, (P∩P)=bidentate phosphine ligand, An=anion] have already been described as luminescent materials and have also already been used in opto-electronic components. The novel feature of the metal complexes of the formulae VII and VIII is the neutrality, which is why they can advantageously be employed in corresponding applications.

formula VII

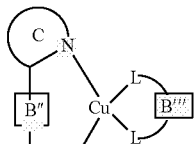

formula VIII

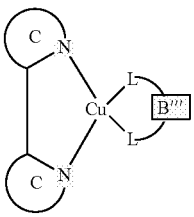

Nitrogen heterocycles are defined as under A), but the bridge B" is neutral. This gives rise to neutral nitrogen ligands, such as, for example:

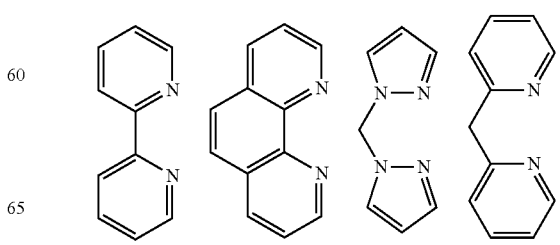

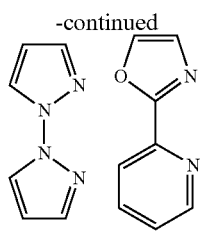

The ligands here may also be substituted by one or more radicals R.

They will be denoted by L-B"-L or N'∩N' below.

L is likewise defined as under A). B''' is a mononegatively charged bridge, such as $R_2B(CH_2)_2$ or carborane. Examples of mononegatively charged phosphine ligands can therefore be the following:

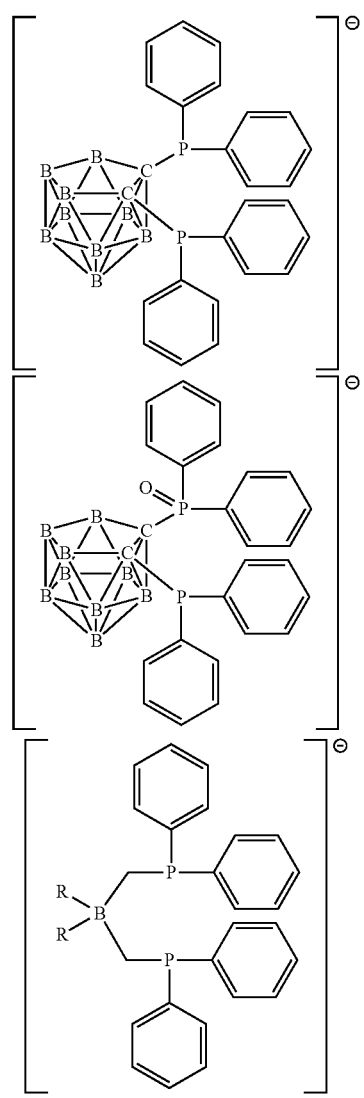

The ligands here may also be substituted by one or more radicals R.

The above-mentioned neutral and mononegatively charged nitrogen and phosphine ligands are already known from the coordination chemistry of the transition metals. U.S. Pat. No. 6,649,801 B2 (J. C. Peters et al.) and U.S. Pat. No. 5,627,164 (S. Gorun et al.) have described some zwitterionic transition-metal complexes with boron-containing ligands as potential catalysts. Since the excited states of the N-heteroaromatic groups (in particular pyrazolyl groups) and those of the phosphine and arsine ligands are energetically very high, these ligands are frequently used as auxiliary ligands (i.e. they are not involved in the $T_1$-$S_0$ transition which is responsible for the emission) in luminescent transition-metal complexes. The patents WO 2005118606 (H. Konno), CN 1624070 A (Z. H. Lin) and US 20020182441 A1 (M. E. Thompson et al.) comprehensively describe Ir(III), Pt(II), Os(II) complexes as emitters which contain cyclometallating ligands of the 2-phenylpyridine type as chromophores and pyrazolylborates as auxiliary ligands.

The combination described of A) mononegatively charged nitrogen ligands N—B—N (or N—B"—N and N∩N) and neutral ligands L or L-B'-L and of B) neutral ligands N—B"—N (or N'∩N') and mononegatively charged ligands L-B'''-L in a metal complex with a tetracoordinated Cu(I) central ion surprisingly results in strongly photoluminescent materials. Both the metal atom and the (hetero)aromatic moieties of the two ligands N—B—N (or N—B"—N, N∩N) and L-B'-L or N—B"—N (or N'∩N') and L-B'''-L are involved in the electronic transition on which the emission is based and which is associated with the HOMO-LUMO transition. This is illustrated in FIG. 4, which shows by way of example the limiting orbitals for a complex.

C) Complexes with a Bridge Between the N Ligand and L

Preference is given to neutral complexes of the formula IX:

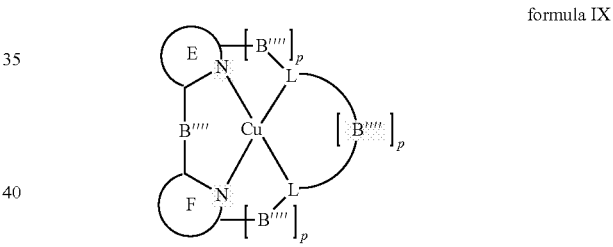

formula IX

In this formula, the N heterocycles denoted by E and F have, independently of one another, the same meaning as the heterocycles denoted by A, B, C or D above. B'''' has, independently of one another, the same meaning as the above-mentioned bridges B, B', B" or B''' or may also stand for a single bond. The index p stands, independently of one another, for 0, 1, 2 or 3, preferably for 0, 1 or 2, particularly preferably for 0 or 1, where at least one index p which describes a bridge between an N heterocycle and L is not equal to 0. p=0 here means that no bridge B'''' is present. In order to obtain neutral complexes, the charges of the N heterocycles denoted by E and F and of the bridges B'''' must be selected appropriately so that the charges compensate for the charge of the Cu(I) ion.

As stated above, the compounds according to the invention are used in an electronic device. An electronic device here is taken to mean a device which comprises at least one layer which comprises at least one organic compound. However, the component may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers), OLED sensors, in particular gas and vapour sensors which are not hermetically screened from the outside, and organic plasmon emitting devices (D. M. Koller et al., *Nature Photonics* 2008, 1-4), but preferably organic electroluminescent devices (OLEDs).

The organic electroluminescent device comprises a cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

In a preferred embodiment of the invention, the complexes of the formulae A and I to IX according to the invention are employed as triplet emitters in an emitter layer of a light-emitting opto-electronic component. In particular through a suitable combination of the ligands N—B—N (or N—B"—N and N∩N) and L or L-B'-L, emitter substances can also be obtained for blue emission colours (see below, Examples 1-3), where, on use of other ligands having lower-lying triplet states, it is also possible to synthesise light-emitting Cu(I) complexes having other emission colours (green, red) (see also Example 4).

The complexes of the formulae A and I to IX can, in accordance with the invention, also be employed as absorber materials in an absorber layer of an opto-electronic component, for example in organic solar cells.

The proportion of the copper(I) complex in the emitter or absorber layer in an opto-electronic component of this type is 100% in an embodiment of the invention. In an alternative embodiment, the proportion of the copper(I) complex in the emitter or absorber layer is 1% to 99%.

The concentration of the copper(I) complex as emitter in optical light-emitting components, in particular in OLEDs, is advantageously between 1% and 10%.

Suitable matrix materials which can be used in combination with the copper(I) complex are preferably selected from aromatic ketones, aromatic phosphine oxides and aromatic sulfoxides and sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl) and the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles and boronic esters, for example in accordance with WO 06/117052, triazine derivatives, for example in accordance with the unpublished application DE 102008036982.9, WO 07/063754 or WO 08/056746, zinc complexes, for example in accordance with EP 652273 or WO 09/062578, and diazasilol and tetraazasilol derivatives, for example in accordance with the unpublished application DE 102008056688.8. It may also be preferred to use a mixture of two or more of these matrix materials, in particular of at least one hole-transporting matrix material and at least one electron-transporting matrix material.

It is also possible to use the compounds according to the invention in another layer of the organic electroluminescent device, for example in a hole-injection or -transport layer or in an electron-transport layer. Due to the comparatively easy oxidisability of the copper(I) ion, the materials are also particularly suitable as hole-injection or hole-transport material.

In general, all further materials which are usually used in the area of organic semiconductors, in particular in the area of organic electroluminescent devices, for example hole-injection and -transport materials, electron-injection and -transport materials, hole-blocking materials, exciton-blocking materials, etc., can be employed in accordance with the invention for the other layers. The person skilled in the art can therefore employ all materials known for organic electroluminescent devices in combination with the compounds according to the invention without inventive step.

The present invention also relates to electronic devices, in particular the electronic devices mentioned above, which comprise a copper(I) complex described here. The electronic component here can preferably be in the form of an organic light-emitting component, an organic diode, an organic solar cell, an organic transistor, an organic light-emitting diode, a light-emitting electrochemical cell, an organic field-effect transistor or an organic laser.

Preference is furthermore given to an electronic device, in particular an organic electroluminescent device, characterised in that one or more layers are applied by means of a sublimation process, in which the materials are applied by vapour deposition in vacuum sublimation units at an initial pressure of below $10^{-5}$ mbar, preferably below $10^{-6}$ mbar. However, it is also possible for the initial pressure to be even lower, for example below $10^{-7}$ mbar.

Preference is likewise given to an electronic device, in particular an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an electronic device, in particular an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, for example, by suitable substitution, are required for this purpose. The application can also be carried out by wet-chemical methods by means of a colloidal suspension. If the application is carried out by wet-chemical methods by means of a colloidal suspension, the particle size is preferably <10 nm, particularly preferably <1 nm.

These processes are generally known to the person skilled in the art and can be applied by him without inventive step to organic electroluminescent devices comprising the compounds according to the invention. Hybrid processes, in which a plurality of the above-mentioned processes are combined for different layers, are likewise possible. The present invention likewise relates to these processes.

The compounds according to the invention are very highly suitable for use in electronic devices and result, in particular on use in an organic electro-luminescent device, in high efficiencies, long lifetimes and good colour coordinates.

FIGURES

Advantageous embodiments arise, in particular, from the copper(I) complexes according to the invention shown in the figures and the experimental data obtained using them. The drawings show the following:

FIG. 4 shows photoluminescence spectra of [Cu(H$_2$Bpz$_2$)(pop)] investigated as pure polycrystalline material (a) and as dopant in a PMMA film (b);

FIG. 11 shows an example of an OLED device having an emitter layer comprising a copper complex according to the invention, which can be applied by wet-chemical methods (the layer thickness data are illustrative values);

FIG. 12 shows an example of an OLED device which can be produced by means of the vacuum sublimation technique, comprising complexes according to the invention in the emitter layer; and FIG. 13 shows an example of a differentiated, highly efficient OLED device comprising a sublimable copper complex according to the invention as emitter material.

REFERENCES

Figure 1:
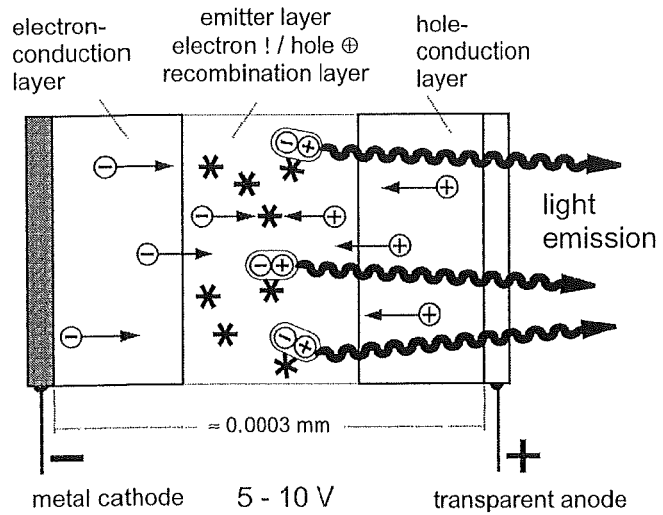
FIG. 1 shows a diagrammatic and simplified representation of the mode of functioning of an OLED (the applied layers only have a thickness of, for example, about 300 nm)
Figure 2:
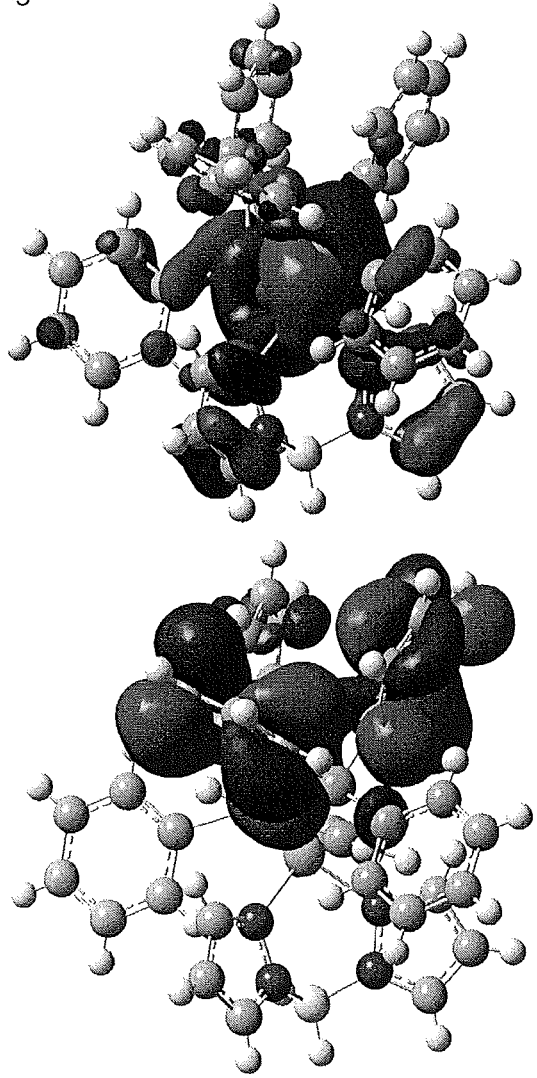
FIG. 2 shows limiting orbital contours: HOMO (left) and LUMO (right) of [Cu(pz$_2$BH$_2$)(pop)] (see Example 1) (the DFT calculations were carried out at the B3LYP/LANL2DZ theory level. The starting geometry used was the crystal structure of [Cu(pz$_2$BH$_2$)(pop)])

[i] C. Adachi, M. A. Baldo, S. R. Forrest, S. Lamansky, M. E. Thompson, R. C. Kwong, *Appl. Phys. Lett.* 2001, 78, 1622.

[ii] X. H. Yang, D. C. Müller, D. Neher, K. Meerholz, *Adv. Mater.* 2006, 18, 948; X. H. Yang, D. Neher, *Appl. Phys. Lett.* 2004, 84, 2476.

[iii] J. Shinar (ed.), *Organic light-emitting devices—A survey*, AIP-Press, Springer, New York, 2004.

[iv] H. Yersin, *Top. Curr. Chem.* 2004, 241, 1.

[v] H. Yersin (ed.), *Highly Efficient OLEDs with Phosphorescent Materials*, Wiley-VCH, Weinheim 2008.

[vi] Z. H. Kafafi, *Organic Electroluminescence*, Taylor & Francis, Boca Raton, 2005.

[vii] M. E. Thompson, P. I. Djurovich, J. Li (University of Southern California, Los Angeles, Calif.), WO 2004/017043 A2, 2004.

[viii] M. E. Thompson, P. I. Djurovich, R. Kwong (University of Southern California, Los Angeles, Calif., Universal Display Corp, Ewing, N.Y.), WO 2004/016711 A1, 2004.

[ix] A. Tsuboyama, S. Okada, T. Takiguchi, K. Ueno, S. Igawa, J. Kamatani, M. Furugori, H. Iwawaki (Canon KK, Tokyo), WO 03/095587 A1, 2003.

[x] C.-M. Che, US 2003/0205707 A1, 2003.

[xi] C.-M. Che, W. Lu, M. C.-W. Chan, US 2002/0179885 A1, 2002.

[xii] J. Kamatani, S. Okada, A. Tsuboyama, T. Takiguchi, S. Igawa, US 2003/186080 A1, 2003.

[xiii] P. Stößel, I. Bach, A. Büsing (Covion Organic Semiconductors GmbH), DE 10350606 A1, 2005.

[xiv] M. Bold, C. Lennartz, M. Egen, H.-W. Schmidt, M. Thelakkat, M. Bäte, C. Neuber, W. Kowalsky, C. Schildknecht (BASF AG), DE 10338550 A1, 2005.

[xv] C. Lennartz, A. Vogler, V. Pawlowski (BASF AG), DE 10358665 A1, 2005.

[xvi] B. Hsieh, T. P. S. Thorns, J. P. Chen (Canon KK, Tokyo), US 2006/989273 B2, 2006.

[xvii] N. Schulte, S. Heun, I. Bach, P. Stoessel, K. Treacher (Covion Organic Semiconductors), WO 2006/003000 A1, 2006.

[xviii] A. Vogler, V. Pawlowski, H.-W. Schmidt, M. Thelakkat (BASF AG), WO 2006/032449 A1, 2006.

[xix] T. K. Hatwar, J. P. Spindler, R. H. Young (Eastman Kodak Co), WO 2006/028546 A1, 2006.

[xx] P. A. Breddels, P. A. M. Berdowski, G. Blasse, D. R. McMillin, *J. Chem. Soc., Faraday Trans.* 1982, 78, 595; S.-M. Kuang, D. G. Cuttell, D. R. McMillin, P. E. Fanwick, R. A. Walton, *Inorg. Chem.* 2002, 41, 3313; D. G. Cuttel, S.-M. Kuang, P. E. Fanwick, D. R. McMillin, R. A. Walton, *J Am. Chem. Soc.* 2002, 124, 6.

[xxi] K. R. Kyle, C. K. Ryu, J. A. DiBenedetto, P. C. Ford, *J. Am. Chem. Soc.* 1991, 113, 2954; H. Araki, K. Tsuge, Y. Sasaki, S. Ishizaka, N. Kitamura, *Inorg. Chem.* 2005, 44, 9667.

[xxii] A. Tsuboyama, K. Kuge, M. Furugori, S. Okada, M. Hoshino, K. Ueno, *Inorg. Chem.* 2007, 46, 1992.

[xxiii] M. T. Buckner, D. R. McMillin, *J. C. S. Chem. Comm.,* 1978, 759; R. A. Rader, D. R. McMillin, M. T. Buckner, T. G. Matthews, D. J. Casadonte, R. K. Lengel, S. B. Whittaker, L. M. Darmon, F. E. Lytle, *J. Am. Chem. Soc.* 1981, 103, 5906; C. E. A. Palmer, D. R. McMillin, *Inorg. Chem.* 1987, 26, 3837.

[xxiv] C.-L. Chan, K.-L. Cheung, W. H. Lam, E. C.-C. Cheng, N. Zhu, S. W.-K. Choi, V. W.-W. Yam, *Chem. Asian J.* 2006, 1-2, 273.

[xxv] V. Palowski, G. Knör, C. Lennartz, A. Vogler, *Eur. J. Inorg. Chem.* 2005, 3167.

[xxvi] M. I. Bruce, N. N. Zaitseva, B. W. Skelton, N. Somers, A. H. White, *Inorg. Chim. Acta* 2007, 360, 681.

[xxvii] Y. Ma, C.-M. Che, H.-Y. Chao, X. Zhou, W.-H. Chan, J. Shen, *Adv. Mater.* 1999, 11, 852.

[xxviii] Q. Zhang, Q. Zhou, Y. Cheng, L. Wang, D. Ma, X. Jing, F. Wang, *Adv. Mater.* 2004, 16, 432; N. Armaroli, G. Accorsi, M. Holler, O. Moudam, J.-F. Nierengarten, Z. Zhou, R. T. Wegh, R. Welter, *Adv. Mater.* 2006, 18, 1313.

[xxix] Q. Zhang, Q. Zhou, Y. Cheng, L. Wang, D. Ma, X. Jing, F. Wang, *Adv. Funct. Mater.* 2006, 16, 1203; Q. Zhang, J. Ding, Y. Cheng, L. Wang, Z. Xie, X. Jing, F. Wang, *Adv. Funct. Mater.* 2007, 17, 2983.

EXAMPLES

The invention is now explained by means of examples with reference to figures, without wishing it to be restricted thereby. The person skilled in the art will be able to carry out the invention throughout the range disclosed from the descriptions and prepare further complexes according to the invention without inventive step and use them in electronic devices or use the process according to the invention.

Example 1

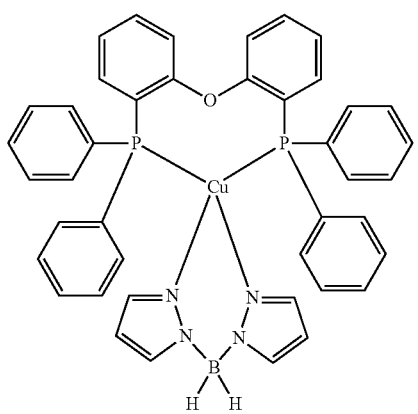

[Cu(H$_2$Bpz$_2$)(pop)]

Preparation

A solution of [Cu(CH$_3$CN)$_4$](PF$_6$) (0.186 g, 0.500 mmol) and bis(2-diphenyl-phosphinophenyl)ether (pop, 0.269 g, 0.500 mmol) in acetonitrile (15 ml) is stirred for 30 min. under an argon atmosphere. K[H$_2$Bpz$_2$] (0.093 g, 0.500 mmol) is then added to the solution, and the resultant mixture is stirred for a further 2 hours under an argon atmosphere. The resultant white precipitate is filtered off and washed three times with 5 ml of acetonitrile. Yield 0.313 g, 84%.

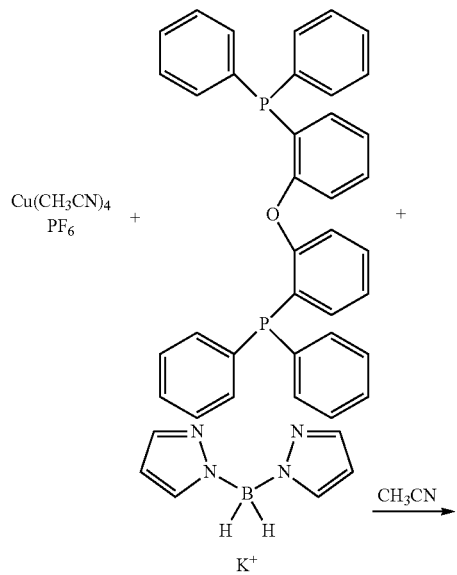

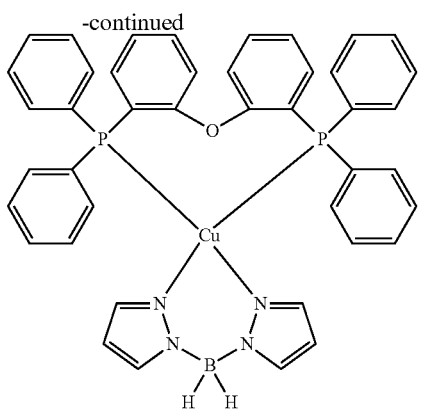

$^1$H-NMR (CDCl$_3$, 298 K): δ 7.59 (d, 2H), 7.05-7.22 (m, br, 20H), 6.78-6.87 (m, br, 6H), 6.68-6.71 (m, br, 2H), 5.84 (t, 2H), 5.30 (s, 2H). $^{13}$C{$^1$H}-NMR: δ 128.2, 129.2, 130.6, 132.8, 134.0, 134.3, 140.1. $^{31}$P{$^1$H}-NMR: δ −17.23 (s), −18.75 (s). ES-MS: m/e=749.3 (MH$^+$, 100.0%), 750.3 (58.0%), 748.2 (24.0%), 752.3 (21.5%), 753.3 (4.8%). EA: found C, 61.72; H, 4.52; N, 6.72%; calc. C, 61.93; H, 4.59; N, 6.72 (for C$_{43}$H$_{38}$BCuN$_4$OP$_2$Cl$_2$).

Crystal Structure

Figure 3:
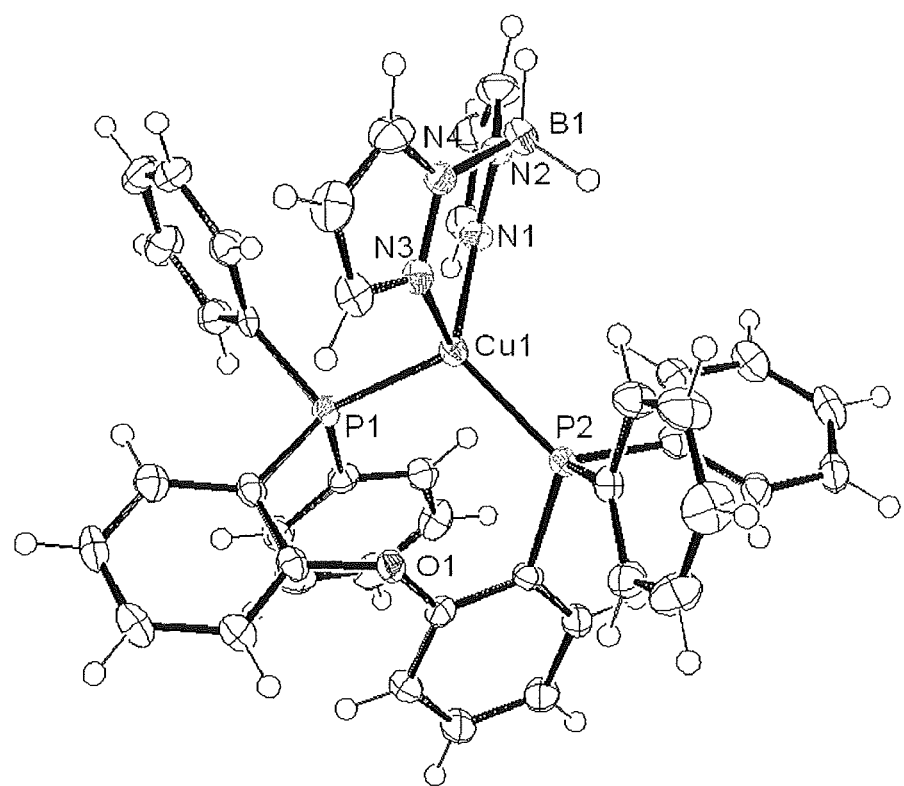
FIG. 3 shows an ORTEP image of a [Cu(H$_2$Bpz$_2$)(pop)] molecule.

An ORTEP image of this complex is shown in FIG. 3.

Photoluminescence Properties

The photoluminescence properties of this complex are shown in FIG. 4.

Example 2

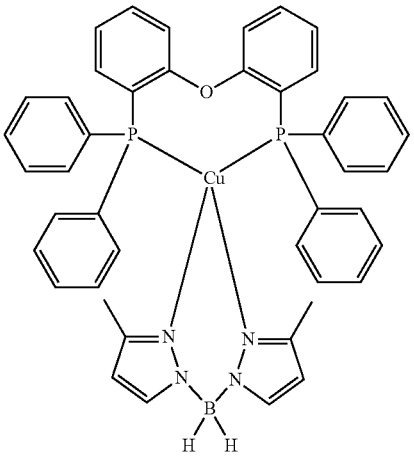

[Cu(H$_2$B(5-Me-pz)$_2$)(pop)]

Preparation

The synthetic route is analogous to [Cu(H$_2$Bpz$_2$)(pop)] (Example 1). Yield 81%. $^1$H-NMR (CDCl$_3$, 298 K): δ 7.52 (d, 2H), 7.35-7.29 (m, br, 10H), 7.22 (d, 4H), 7.12 (t, 8H), 6.99 (td, 2H), 6.86 (td, 2H), 6.72-6.67 (m, br, 2H), 6.61-6.58 (m, 2H), 5.76 (d, 2H), 1.46 (s, 6H). $^{13}$C{$^1$H}-NMR: δ 14.07, 103.1, 119.6, 124.1, 128.1, 128.2, 129.2, 130.4, 132.5, 132.6, 133.8, 133.4, 134.5, 134.7, 135.4, 148.9, 157.0. $^{31}$P{$^1$H}-NMR: δ 14.89 (s), −16.18 (s), −17.14 (s). ES-MS: m/e=MH$^+$, 772.2 (100.0%), 778.2 (57.0%), 780.2 (22.2%), 781.2 (6.8%). EA: found C, 68.45; H, 5.10; N, 7.33%; calc. C, 68.00; H, 5.19; N, 7.21 (for C$_{49}$H$_{43}$BCuN$_8$OP$_2$Cl$_2$).

Crystal Structure

Figure 5:
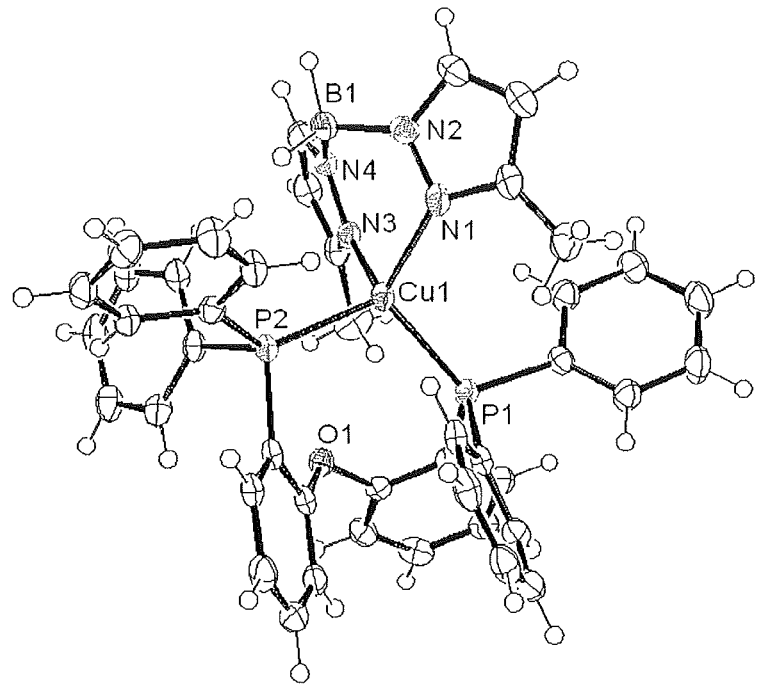
FIG. 5 shows an ORTEP image of a [Cu(H$_2$B(5-Me-pz)$_2$)(pop)] molecule.

An ORTEP image of this complex is shown in FIG. 5.

Photoluminescence Properties

Figure 6:
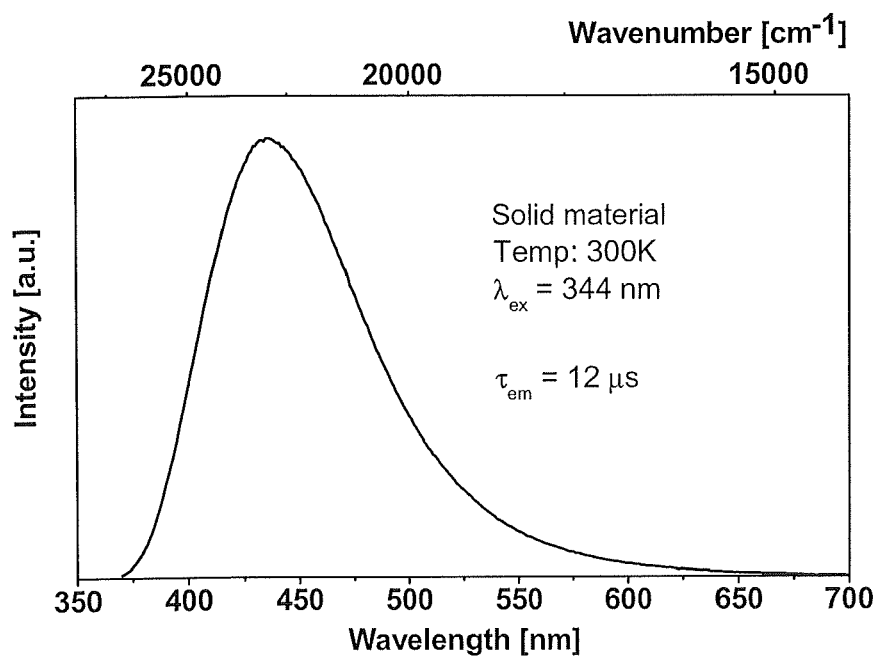
FIG. 6 shows a photoluminescence spectrum of [Cu(H$_2$B(5-Me-pz)$_2$)(pop)] as pure polycrystalline material.

The photoluminescence properties of this complex are shown in FIG. 6.

Example 3

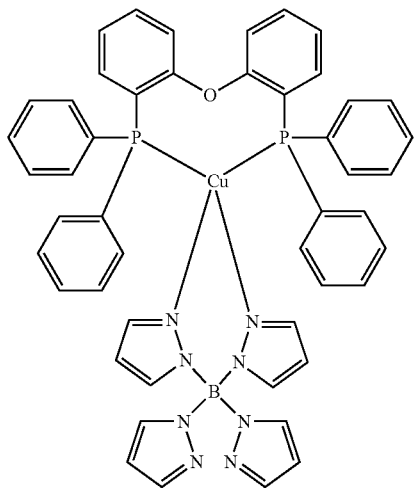

[Cu(Bpz₄)(pop)]

Preparation

The synthetic route is analogous to [Cu(H₂Bpz₂)(pop)] (Example 1). Yield 79%. ¹H-NMR (CDCl₃, 298 K): δ 7.38 (br, 4H), 7.05-7.24 (m, br, 20H), 6.76-6.98 (m, br, 6H), 6.68-6.71 (m, br, 2H), 5.85 (t, 4H), 5.30 (s, 4H). ¹³C{¹H}-NMR: δ 104.4, 106.3, 120.3, 124.4, 124.8, 126.4, 128.2, 128.3, 128.5, 128.6, 129.3, 129.7, 130.8, 131.5, 131.6, 131.8, 132.0, 133.2, 133.3, 133.4, 133.8, 134.0, 134.1, 135.3, 135.9, 141.7, 157.8, 157.9, 158.1. ³¹P{¹H}-NMR: δ −14.37 (s). ES-MS: m/e=881.4 (MH⁺, 100.0%), 882.4 (63.0%), 883.4 (59.0%), 884.3 (26.1%), 880.4 (23.0%), 885.4 (6.3%), 886.3 (1.4%). EA: found C, 61.55; H, 4.48; N, 11.63%; calc. C, 60.85; H, 4.48; N, 11.59 (for C₄₉H₄₃BCuN₈OP₂Cl₂).

Crystal Structure

Figure 7:
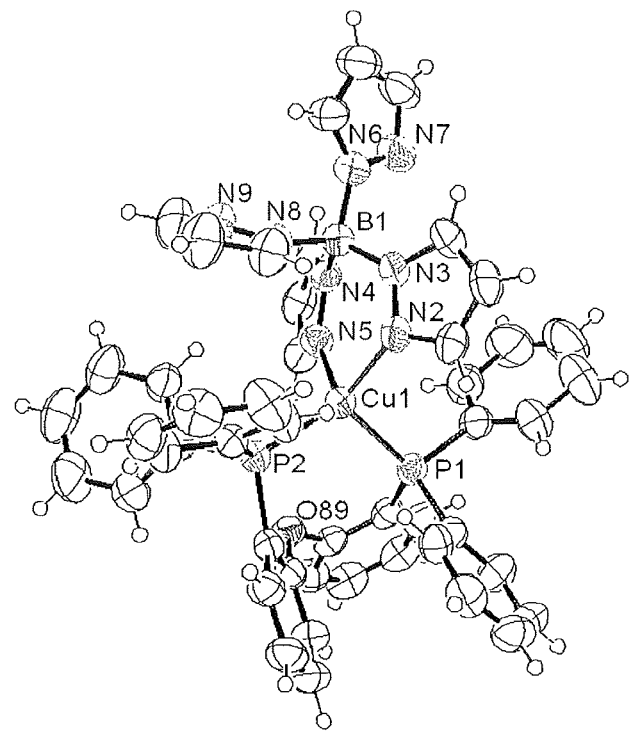
FIG. 7 shows an ORTEP image of a [Cu(Bpz$_4$)(pop)] molecule.
Figure 8:
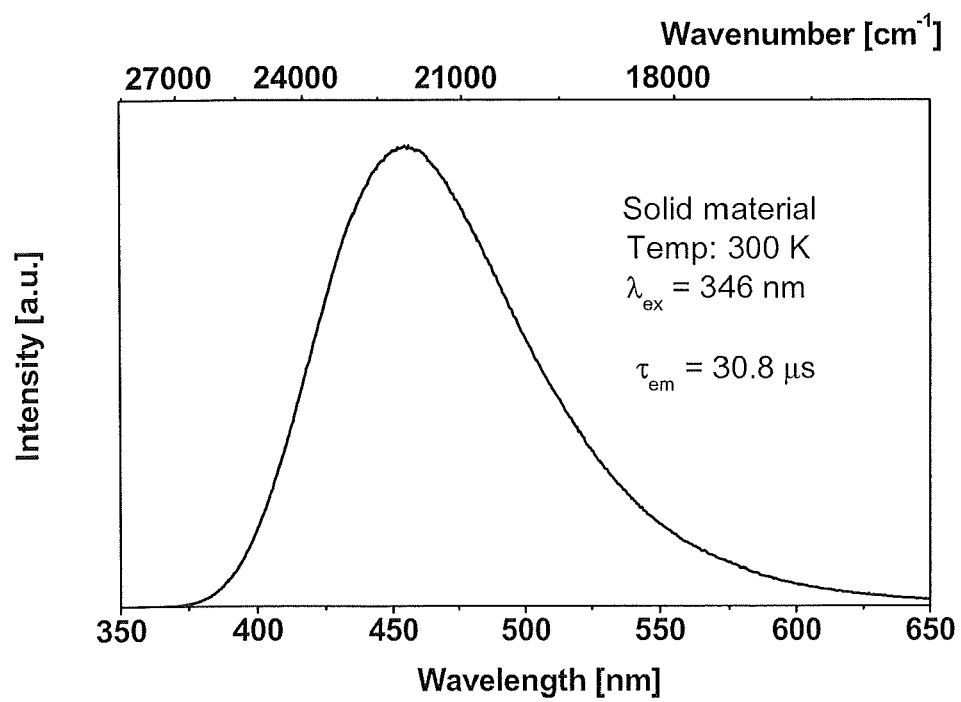
FIG. 8 shows a photoluminescence spectrum of [Cu(Bpz$_4$)(pop)] as pure polycrystalline material.

An ORTEP image of this complex is shown in FIG. 7.

Photoluminescence Properties

The photoluminescence spectrum of this complex is shown in FIG. 5.

Example 4

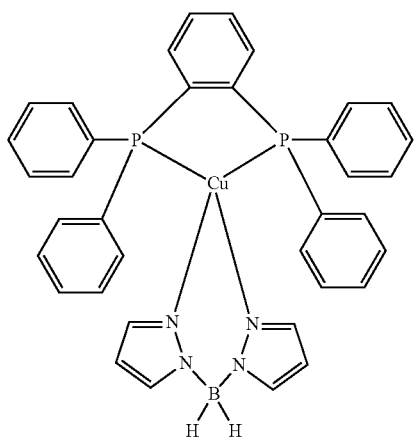

[Cu(H₂Bpz₂)(dppb)]

Synthetic Route

The synthetic route is analogous to [Cu(H₂Bpz₂)(pop)] (Example 1). Yield 80%. ¹H-NMR (CDCl₃, 298 K): δ 7.38 (br, 4H), 7.05-7.24 (m, br, 20H), 6.76-6.98 (m, br, 6H), 6.68-6.71 (m, br, 2H), 5.85 (t, 4H), 5.30 (s, 4H). ¹³C{¹H}-NMR: δ 103.0, 128.4, 128.5, 128.6, 128.9, 129.0, 129.2, 130.3, 132.5, 132.9, 133.0, 133.1, 133.8, 134.1, 134.3, 134.5, 134.6, 134.7, 139.9, 142.7, 143.2, 143.6. ³¹P{¹H}-NMR: δ −1.96 (s), −7.37 (s). ES-MS: m/e=657.1 (MH⁺, 100.0%), 658.1 (52.4%), 656.1 (34.6%), 660.1 (14.1%), 661.1 (4.2%). EA: found: C, 65.42; H, 4.86; N, 8.42%; calc.: C, 65.81; H, 4.91; N, 8.53 (for C₄₉H₄₃BCuN₈OP₂).

Crystal Structure

Figure 9:
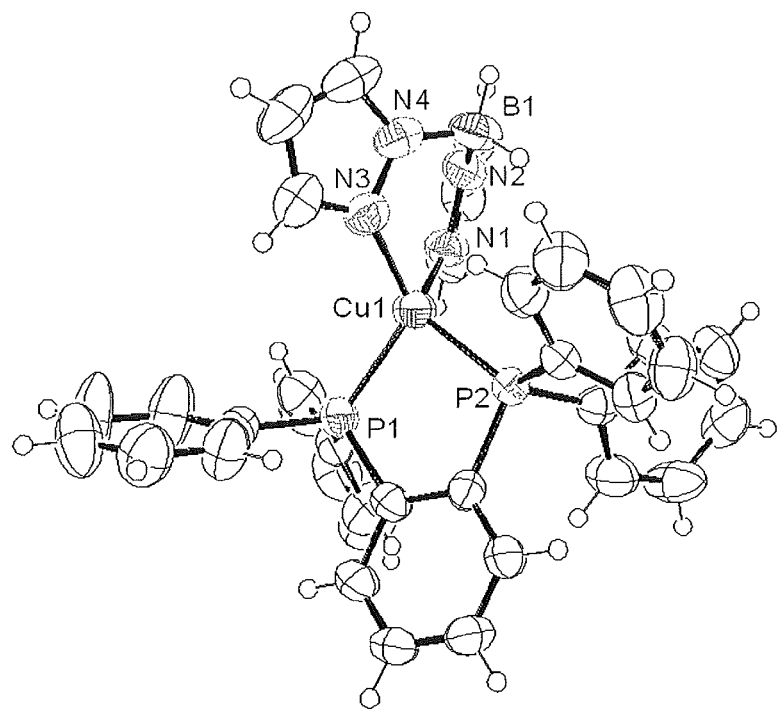
FIG. 9 shows an ORTEP image of a [Cu(H$_2$Bpz$_2$)(dppb)] molecule.

An ORTEP image of this complex is shown in FIG. 9.

Photoluminescence Properties

Figure 10:
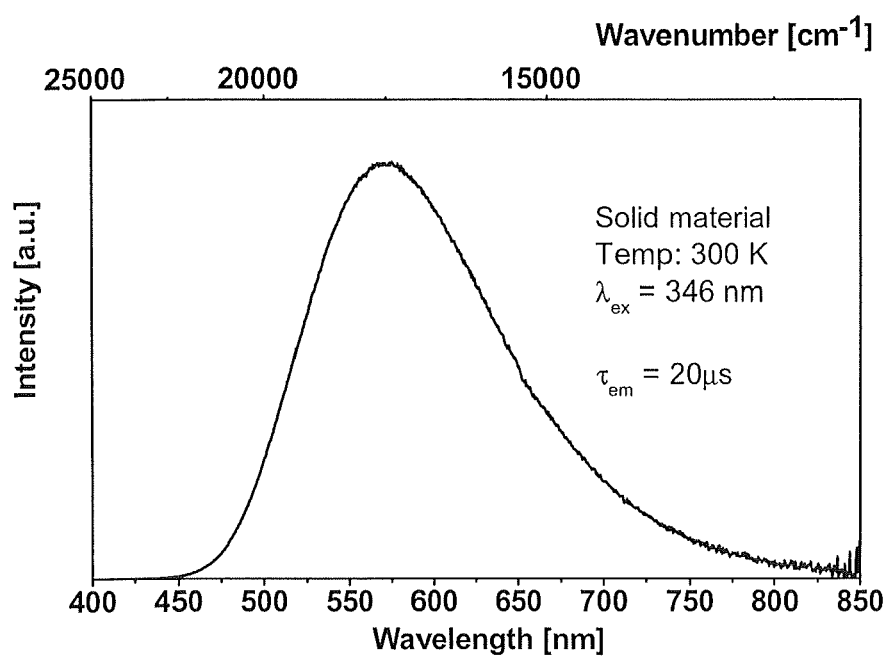
FIG. 10 shows a photoluminescence spectrum of [Cu(Bpz$_4$)(pop)] as pure polycrystalline material.

The photoluminescence spectrum of [Cu(Bpz₄)(pop)] as pure polycrystalline material is shown in FIG. 10.

Example 5

OLED Devices

The copper complexes according to the invention can be used as emitter substances in an OLED device. For example, good power efficiencies can be achieved in a typical OLED layer structure consisting of an ITO anode, a hole conductor comprising PEDOT/PSS, the emitter layer according to the invention, optionally a hole-blocking layer, an electron-conductor layer, a thin LiF or CsF interlayer for improving electron injection and a metal electrode (cathode). These various layers having a total thickness of a few 100 nm can be applied, for example, to a glass substrate or another support material. A corresponding sample device is shown in FIG. 11.

The meaning of the layers shown in FIG. 11 is as follows:

1. The support material used can be glass or any other suitable solid or flexible transparent material.
2. ITO=indium tin oxide.
3. PEDOT/PSS=polyethylenedioxythiophene/polystyrenesulfonic acid. This is a hole-conductor material (HTL=hole transport layer) which is water-soluble.
4. Emitter layer, frequently abbreviated to EML, comprising an emitter substance according to the invention. This material can be dissolved, for example, in organic solvents, which enables dissolution of the underlying PEDOT/PSS layer to be prevented. The emitter substance according to the invention is used in a concentration which prevents or greatly restricts self-quenching processes or triplet-triplet annihilations. Concentrations greater than 2% and less than 12% have proven highly suitable.
5. ETL=electron-transport material. For example, vapour-depositable Alq₃ can be used. The thickness is, for example, 40 nm.
6. The very thin interlayer of, for example, CsF or LiF reduces the electron-injection barrier and protects the ETL layer. This layer is generally applied by vapour deposition. For a further simplified OLED structure, the ETL and CsF layers can optionally be omitted.
7. The conductive cathode layer is applied by vapour deposition. Al represents an example. It is also possible to use Mg:Ag (10:1) or other metals.

The voltage applied to the device is, for example, 3 to 15 V. Further embodiments are shown by FIGS. 12 and 13, in which OLED devices comprising the emitter substances according to the invention are produced by means of the vacuum sublimation technique.

The meaning of the layers shown in FIG. 13 is as follows:

1. The support material used can be glass or any other suitable solid or flexible transparent material.
2. ITO=indium tin oxide.
3. HTL=hole transport layer. α-NPD, for example, in a thickness of, for example, 40 nm can be employed for this purpose. The structure shown in FIG. 13 can be supplemented by a suitable further layer between layers 2 and 3, which improves hole injection (for example copper phthalocyanine (CuPc, for example 10 nm in thickness)).
4. The electron-blocking layer is intended to ensure that electron transport to the anode is suppressed since this current would only cause ohmic losses (thickness, for example, 30 nm). This layer can be omitted if the HTL layer is already intrinsically a poor electron conductor.
5. The emitter layer comprises or consists of the emitter material according to the invention. For sublimable materials according to the invention, this can be applied by sublimation. The layer thickness can be, for example, between 50 nm and 200 nm. For emitter materials according to the invention which emit in the green or red, the common matrix materials, such as CBP (4,4'-bis(N-carbazolyl)biphenyl), are suitable. For emitter materials according to the invention which emit in the blue, UHG matrix materials (see, for example, M. E. Thompson et al., Chem. Mater. 2004, 16, 4743) or other so-called wide-gap matrix materials can be employed.
6. The hole-blocking layer is intended to reduce ohmic losses caused by hole currents to the cathode. This layer can, for example, have a thickness of 20 nm. A suitable material is, for example, BCP (4,7-diphenyl-2,9-dimethylphenanthroline=bathocuproin).
7. ETL=electron-transport material. For example, vapour-depositable Alq$_3$ can be used. The thickness is, for example, 40 nm.
8. The very thin interlayer of, for example, CsF or LiF reduces the electron-injection barrier and protects the ETL layer. This layer is generally applied by vapour deposition.
9. The conductive cathode layer is applied by vapour deposition. Al represents an example. It is also possible to use Mg:Ag (10:1) or other metals.

The voltage applied to the device is, for example, 3 V to 15 V.

Example 6

Production and Characterisation of Organic Electroluminescent Devices from Solution LEDs are produced by the general process outlined below. In individual cases, this is adapted to the particular circumstances (for example layer-thickness variation in order to achieve optimum efficiency or colour).
General Process for the Production of OLEDs:
The production of such components is based on the production of polymeric light-emitting diodes (PLEDs), which has already been described many times in the literature (for example in WO 2004/037887 A2). In the present case, the compounds according to the invention are dissolved in toluene, chlorobenzene or DMF together with the matrix materials or matrix-material combinations mentioned. The typical solids content of such solutions is between 10 and 25 g/l if, as here, the layer thickness of 80 nm which is typical for a device is to be achieved by means of spin coating. OLEDs having the following structure are produced analogously to the abovementioned general process:
PEDOT 20 nm (spin-coated from water; PEDOT purchased from BAYER AG; poly[3,4-ethylenedioxy-2,5-thiophene])
Matrix+emitter 80 nm, 10% by weight of emitter (spin-coated from toluene, chlorobenzene or DMF)
Ba/Ag 10 nm of Ba/150 nm of Ag as cathode.
Structured ITO substrates and the material for the so-called buffer layer (PEDOT, actually PEDOT:PSS) are commercially available (ITO from Technoprint and others, PEDOT:PSS as Clevios Baytron P aqueous dispersion from H. C. Starck).

The structures of an emitter E1 in accordance with the prior art and of the matrices M are depicted below for clarity:

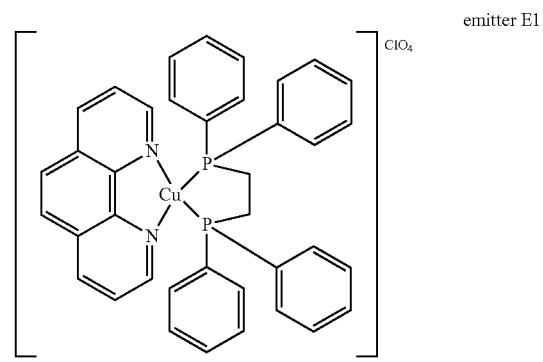

emitter E1
(US 2005/0221115)

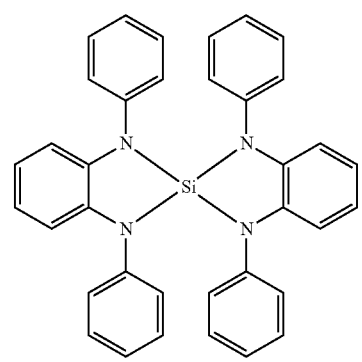

M1
(DE10200856688.8)

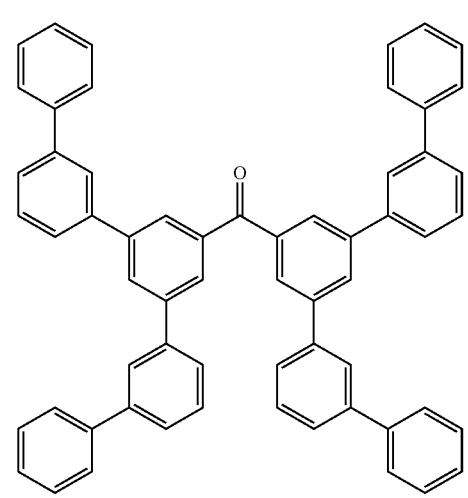

M2
(DE102008033943.1)

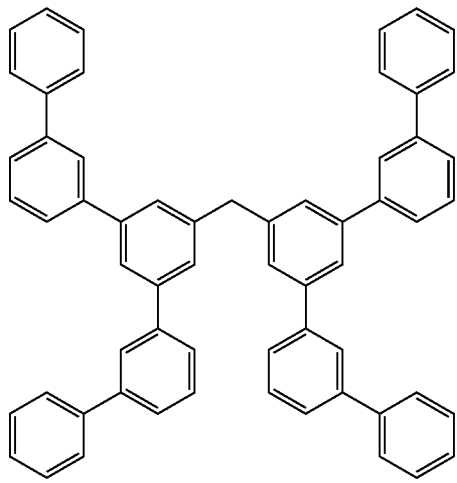

(DE102008033943.1)

The emission layer is applied by spin coating in an inert-gas atmosphere, in the present case argon, and dried by heating at 120° C. for 10 min. Finally, a barium and silver cathode is applied by vacuum vapour deposition. The solution-processed devices are characterised by standard methods; the OLED examples mentioned have not yet been optimised.

Table 1 shows the efficiency and voltage at 100 cd/m² and the colour.

TABLE 1

Device results

| Ex. | Matrix Emitter | EQE at 100 cd/m² [%] | Voltage at 100 cd/m² [V] | CIE x/y |
|---|---|---|---|---|
| Ex. 7 (comparison) | M1 (20%) M3 (70%) Emitter E1 | 4.3 | 8.4 | 0.45/0.49 |
| Ex. 8 | M1 (65%) M3 (25%) Ex. 1 | 5.7 | 5.6 | 0.12/0.26 |
| Ex. 9 | M3 Ex. 2 | 3.0 | 6.5 | 0.11/0.23 |
| Ex. 10 | M2 (55%) M3 (35%) Ex. 3 | 3.5 | 6.3 | 0.12/0.25 |
| Ex. 11 | M1 (20%) M3 (70%) Ex. 4 | 9.3 | 4.8 | 0.46/0.52 |

The invention claimed is:

1. A neutral compound of the formula (II), formula II

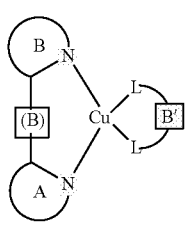

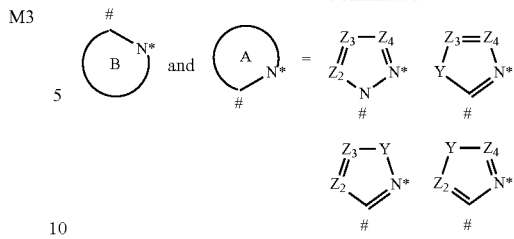

where * denotes the atom which forms the complex bond and # denotes the atom which is bonded to the second unit via B and the following applies to the other symbols used:

L-B'-L, is a bidentate ligand comprising a monodentate phosphanyl or arsanyl ligand L ($R_2E\#$, where E=P or As), which is bonded to a further monodentate ligand L via a bridge B' wherein the radical L is, independently of another, a phosphine or arsine ligand, where one ligand L or both ligands L may also be bonded to A-(B)—B, giving rise to a tetravalent ligand;

$Z_2$-$Z_4$ are on each occurrence, identically or differently, N or CR;

R is on each occurrence selected, identically or differently, from the group consisting of H, D, F, Cl, Br, I, CN, $NO_2$, $N(R^1)_2$, $C(=O)R^1$, $Si(R^1)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, $C=C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, an aromatic or heteroaromatic ring system having 5 to 60 aromatic ring atoms, which may in each ease be substituted by one or more radicals $R^1$, an aryloxy or heteroaryloxy group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;

$R^1$ is on each occurrence selected, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^3$ may form a mono- or polycyclic, aliphatic, aromatic or heteroaromatic ring system with one another;

Y is on each occurrence, identically or differently, O, S or NR;

(B) is $R_2B$, where R has the meaning given above;

B' is an arylene group or —O—, —NR— or —$SiR_2$—.

2. The compound according to claim 1, wherein E in the ligand L is equal to phosphorus.

3. The compound according to claim 1, wherein the substructure A-(B)—B is selected from the group consisting of

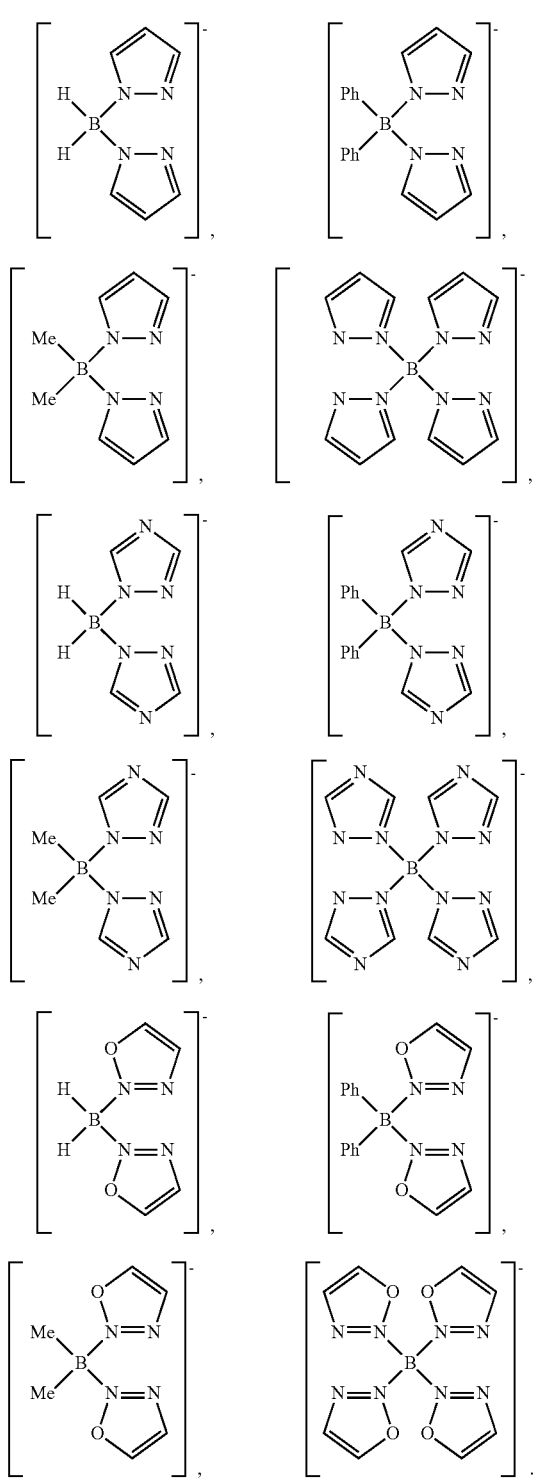

4. The compound according to claim 1, wherein L is selected, independently of one another, from the group consisting of Ph$_2$P, Me$_2$P, Et$_2$P, Ph$_1$MeP, Ph$_1$BnP, (Cyclohexyl)$_2$P, (PhO)$_2$P, (MeO)$_2$P, Ph$_2$As, Me$_2$As, Et$_2$As, PhMeAs, PhBnAs, (Cyclohexyl)$_2$As, where Ph=phenyl, Me=methyl, Et=ethyl, and Bn=benzyl.

5. The compound according to claim 1, wherein L-(B')-L, is selected from the group consisting of

6. An electronic device, selected from the group consisting of organic electroluminescent devices (OLEDs), organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, OLED sensors, gas and vapour sensors which are not hermetically screened from the outside, and organic plasmon emitting devices, comprising one or more of the compounds of the formula (I), (II), (III), (IV) or (VII):

formula I

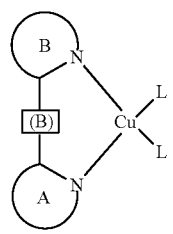

formula II

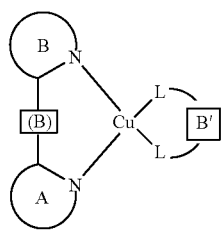

-continued formula III formula IV formula VII where * denotes the atom which forms the complex bond and # denotes the atom which is bonded to the second unit via B or B", $Z_2$-$Z_9$ are on each occurrence, identically or differently, N or CR;

L is, independently of one another, a monodentate phosphine or arsine ligand $R_3E$ (where E=P or As), where one ligand L or both ligands L may also be bonded to A-(B)—B, giving rise to a tetravalent ligand, or, if L is bound to B' or B''', is a bidentate ligand of formula $R_2E$ (where E=P or As);

L-B'-L is a phosphanyl or arsanyl radical, which is bonded to a further radical L via a bridge B' and thus forms a bidentate ligand;

R is on each occurrence selected, identically or differently, from the group consisting of H, D, F, Cl, Br, I, CN, $NO_2$, $N(R^1)_2$, C(=O)$R^1$, Si$(R^1)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C$=$CR^1$, C≡C, Si$(R^1)_2$, Ge$(R^1)_2$, Sn$(R^1)_2$, C=O, C=S, C=Se, C=$NR^1$, P(=O)($R^1$), SO, $SO_2$, $NR^1$, O, S or CON$R^1$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^1$, an aryloxy or heteroaryloxy group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;

$R^1$ is on each occurrence selected, identically or differently, from the group consisting of H, D, F CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^3$ may form a mono- or polycyclic, aliphatic, aromatic or heteroaromatic ring system with one another;

Y is on each occurrence, identically or differently, O, S or NR;

(B) is $R_2B$, where R has the meaning given above;

B' is an alkylene or arylene group or a combination of the two, or —O—, —NR— or —Si$R_2$—;

B" is a neutral bridge, and is on each occurrence, identically or differently, a divalent bridge selected from NR, BR, O, $CR_2$, Si$R_2$, C=NR, C=$CR_2$, S, S=O, $SO_2$, PR and P(=O)R; and B''' is a mononegatively charged bridge.

7. The electronic device according to claim 6, wherein the electronic device comprises one or more compounds of the formula (II).

8. The electronic device according to claim 7, wherein E in the ligand L is equal to phosphorus, where B' is an alkylene or arylene group or a combination of the two, or —O—, —NR— or —Si$R_2$—.

9. The electronic device according to claim 6, wherein the compound is employed as emitter in an emitter layer of a light-emitting opto-electronic component or as absorber material in an absorber layer of an opto-electronic component or as charge-transport material, or as hole-transport material.

10. The electronic device according to claim 6, wherein the compound is employed in combination with a matrix material, where the matrix material is selected from the group consisting of aromatic ketones, aromatic phosphine oxides, aromatic sulfoxides, aromatic sulfones, triarylamines, carbazole derivatives, indolo-carbazole derivatives, azacarbazole, derivatives, bipolar matrix materials, silanes, azaboroles, boronic esters, triazine derivatives, zinc complexes, diaza-silole or tetraaza-silole derivatives, and mixtures of two or more of these matrix materials.

11. A process for the production of an electronic device according to claim 6, wherein one or more layers are applied by means of a sublimation process or in that one or more layers are applied by means of the OVPD (organic vapour phase deposition) process or with the aid of carrier-gas sublimation or in that one or more layers are produced from solution or by means of a printing process.

12. A compound of the formula VII:

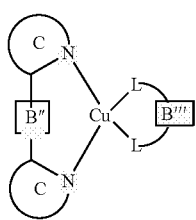

formula VII where
L is a monodentate phosphine or arsine ligand $R_2E$ (where E=P or As);
and where the nitrogen ligands have the following formulae:

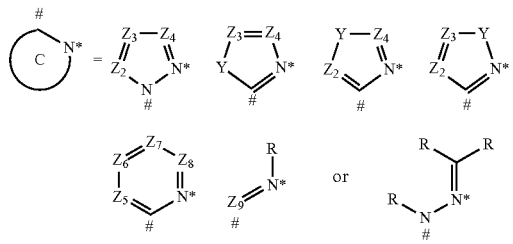

where $Z_2$-$Z_9$ are on each occurrence, identically or differently, N or CR,
where * denotes the atom which forms the complex bond and # denotes the atom which is bonded to the second unit via B and the following applies to the other symbols used:
R is on each occurrence selected, identically or differently, from the group consisting of H, D, F, Cl, Br, I, CN, $NO_2$, $N(R^1)_2$, $C(=O)R^1$, $Si(R^1)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, C≡C, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^1$, an aryloxy or heteroaryloxy group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;

$R^1$ is on each occurrence selected, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^3$ may form a mono- or polycyclic, aliphatic, aromatic or heteroaromatic ring system with one another;

Y is on each occurrence, identically or differently, O, S or NR;

B" is a neutral bridge, and is on each occurrence, identically or differently, a divalent bridge selected from NR, BR, O, $CR_2$, $SiR_2$, C=NR, $C=CR_2$, S, S=O, $SO_2$, PR and P(=O)R; and B''' is a mononegatively charged bridge.

13. The compound of claim 12, wherein B''' is $R_2B(CH_2)_2$ or carhorane.

14. A compound of the formula VIII:

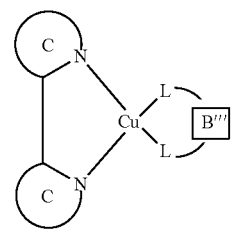

formula VIII where
L is a monodentate phosphine or arsine ligand $R_2E$ (where E=P or As);
and where the nitrogen ligands have the following formulae:

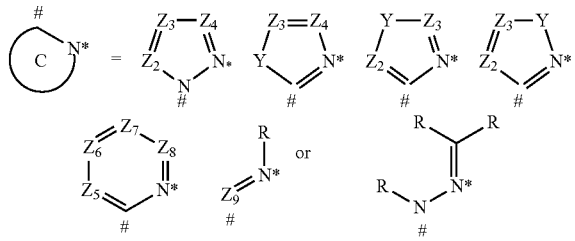

where $Z_2$-$Z_9$ are on each occurrence, identically or differently, N or CR,
where * denotes the atom which forms the complex bond and # denotes the atom which is bonded to the second unit and the following applies to the other symbols used:
R is on each occurrence selected, identically or differently, from the group consisting of H, D, F, Cl, Br, I, CN, $NO_2$, $N(R^1)_2$, $C(=O)R^1$, $Si(R^1)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may he replaced by $R^1C=CR^1$, C≡C, $Si(R^1)_2$, $Ge(R^1)_2$, $Sn(R^1)_2$, C=O, C=S, C=Se, C=NR$^1$, P(=O)(R$^1$), SO, SO$_2$, NR$^1$, O, S or CONR$^1$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^1$, an aryloxy or heteroaryloxy group having 5 to 60 aromatic ring atoms, which may be substituted by one or more radicals R$^1$, or a combination of these systems, where two or more adjacent substituents R may optionally form a monocyclic or polycyclic, aliphatic, aromatic or heteroaromatic ring system, which may he substituted by one or more radicals R$^1$;

R$^1$ is on each occurrence selected, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R$^3$ may form a mono- or polycyclic, aliphatic, aromatic or heteroaromatic ring system with one another;

Y is on each occurrence, identically or differently, O, S or NR; and

B''' is R$_2$B(CH$_2$)$_2$ or carborane.

15. An electronic device, selected from the group consisting of organic electroluminescent devices (OLEDs), organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, OLED sensors, gas and vapour sensors which are not hermetically screened from the outside, and organic plasmon emitting devices, comprising one or more of the compounds of the formula (V) or (VIII):

formula V formula VIII where where * denotes the atom which forms the complex bond and # denotes the atom which is bonded to the second unit, Z$_2$-Z$_9$ are on each occurrence, identically or differently, N or CR;

L is, independently of one another, a monodentate phosphine or arsine ligand R$_3$E (where E=P or As), or when L is bound to B''', forming a bidentate L-B'''-L ligand, L is independently of one another R$_2$E where E=P or As;

R is on each occurrence selected, identically or differently, from the group consisting of H, D, F, Cl, Br, I, CN, NO$_2$, N(R$^1$)$_2$, C(=O)R$^1$, Si(R$^1$)$_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^1$, where one or more non-adjacent CH$_2$ groups may be replaced by R$^1$C=CR$^1$, C=C, Si(R$^1$)$_2$, Ge(R$^1$)$_2$, Sn($^1$)$_2$, C=O, C=S, C=Se, C=NR$^1$, P(=O)(R$^1$), SO, SO$_2$, NR$^1$, O, S or CONR$^1$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^1$, an aryloxy or heteroaryloxy group having 5 to 60 aromatic ring atoms, which may be substituted by one or more radicals R$^1$, or a combination of these systems, where two or more adjacent substituents R may optionally form a monocyclic or polycyclic, aliphatic, aromatic or heteroaromatic ring system, which may be substituted by one or more radicals R$^1$;

R$^1$ is on each occurrence selected, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R$^3$ may form a mono- or polycyclic, aliphatic, aromatic or heteroaromatic ring system with one another;

Y is on each occurrence, identically or differently, O, S or NR;

B''' is a mononegatively charged bridge.

* * * * *